(12) United States Patent
Sano et al.

(10) Patent No.: US 7,779,880 B2
(45) Date of Patent: Aug. 24, 2010

(54) TUBE CONNECTING APPARATUS

(75) Inventors: Hiroaki Sano, Nakakoma-gun (JP); Masaru Nagashimada, Nakakoma-gun (JP); Shinji Ishida, Isehara (JP); Hideya Fujihara, Nirasaki (JP); Satoshi Yamanushi, Nirasaki (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 717 days.

(21) Appl. No.: 10/562,811

(22) PCT Filed: Jul. 1, 2004

(86) PCT No.: PCT/JP2004/009338
§ 371 (c)(1),
(2), (4) Date: Dec. 29, 2005

(87) PCT Pub. No.: WO2005/002832
PCT Pub. Date: Jan. 13, 2005

(65) Prior Publication Data
US 2006/0144525 A1    Jul. 6, 2006

(30) Foreign Application Priority Data
Jul. 4, 2003    (JP) ............................... 2003-192370

(51) Int. Cl.
*B29C 65/02*    (2006.01)
*B29C 65/18*    (2006.01)
*B29C 65/74*    (2006.01)

(52) U.S. Cl. ...................... 156/353; 156/350; 156/359; 156/304.1; 156/304.2; 156/502; 156/503; 156/510; 156/515; 156/518; 156/251

(58) Field of Classification Search ................ 156/250, 156/304.2, 304.6, 353, 359, 502, 503, 350, 156/365, 251, 510, 518
See application file for complete search history.

(56) References Cited

U.S. PATENT DOCUMENTS

| 4,521,263 | A | 6/1985 | Benin et al. |
| 4,647,756 | A | 3/1987 | Willis |
| 5,279,685 | A * | 1/1994 | Ivansons et al. ............. 156/158 |
| 6,463,979 | B1 * | 10/2002 | Sano et al. .................. 156/503 |
| 6,485,593 | B1 | 11/2002 | Christoffersen |

FOREIGN PATENT DOCUMENTS

EP    0 105 587 A1    4/1984

(Continued)

OTHER PUBLICATIONS

International Search Report dated Oct. 12, 2004.

(Continued)

*Primary Examiner*—Mark A Osele
*Assistant Examiner*—Christopher C Caillouet
(74) *Attorney, Agent, or Firm*—Buchanan Ingersoll & Rooney PC

(57) ABSTRACT

A tube connecting apparatus that can carry out self reset operation without giving damage to the apparatus and that safety of an operator is considered. The tube connecting apparatus has an EEPROM memorizing information with respect to a connecting process state of tubes. When electric power is inputted, the apparatus judges whether power supply was shut off during tube connecting operation based upon the information memorized in the EEPROM with respect to the connecting process state of tubes and a detecting result of a wafer 41 according to a wafer position detecting sensor 421, and carries out reset operation. In the reset operation, the apparatus restarts and completes connecting operation (S620 to 632) by heating the wafer again to fuse the tubes adhered to the wafer (S614, 616). Error indication is displayed at a LCD display to secure connecting strength and the like (S634). A locking state is not cancelled during cooling time after heating of the wafer is stopped to secure safety (S628 to S632).

9 Claims, 25 Drawing Sheets

FOREIGN PATENT DOCUMENTS

| | | |
|---|---|---|
| EP | 0 599 057 A1 | 6/1994 |
| EP | 1 048 316 A2 | 11/2000 |
| JP | 60-34455 A | 2/1985 |
| JP | 61-30582 B2 | 7/1986 |
| JP | 4-308731 A | 10/1992 |
| JP | 6-78971 A | 3/1994 |
| JP | 6-26877 U | 4/1994 |
| JP | 6-091010 A | 4/1994 |
| JP | 9-154920 A | 6/1997 |
| JP | 2000-202034 A | 7/2000 |
| JP | 2000-308670 A | 11/2000 |
| JP | 2000-308688 A | 11/2000 |

OTHER PUBLICATIONS

Supplementary European Search Report issued Feb. 5, 2009 in corresponding European Application No. 04 74 6807.

Office Action issued Aug. 17, 2007 in corresponding Canadian Application No. 2,531,408.

Office Action issued Jul. 31, 2007 in corresponding Japanese Application No. 2003-192370 and English language translation.

European Office Action dated Jan. 27, 2010 issued in the corresponding European Patent Application No. 04 746 807.9-1253.

* cited by examiner

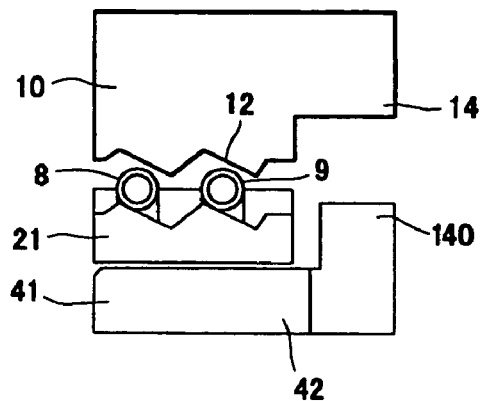
Fig. 2 3 (A)
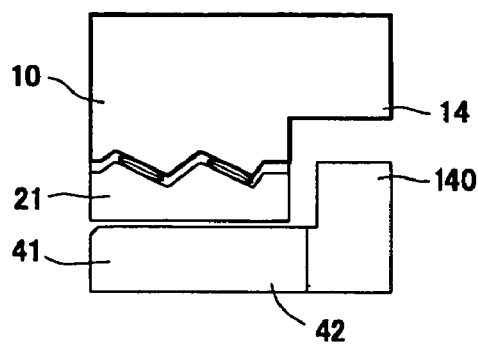
Fig. 2 3 (B)
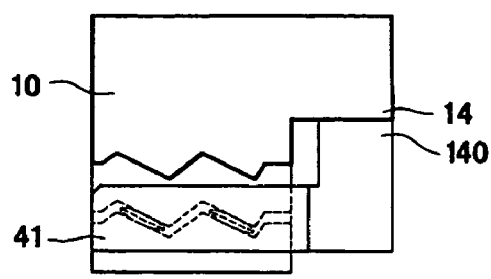
Fig. 2 3 (C)
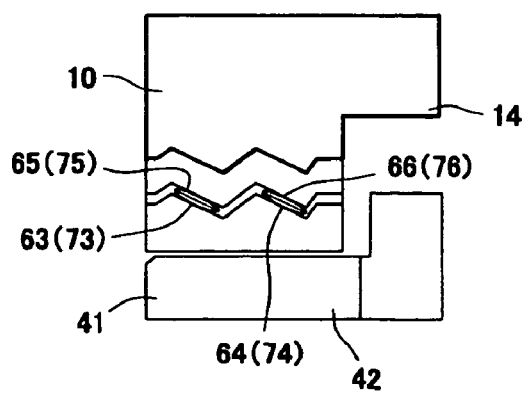
Fig. 2 4

TUBE CONNECTING APPARATUS

FIELD OF THE INVENTION

The present invention relates to a tube connecting apparatus that cuts and then connects flexible tubes, and in particular relates to a tube connecting apparatus equipped with an automatic reset function for a case that power supply is shut off during tube connecting operation and the apparatus stops its operation.

DESCRIPTION OF RELATED ART

Conventionally, in a case that tube connecting between a blood-collecting bag and a blood-component bag in a blood transfusion system, exchanging between a dialytic-fluid bag and a waste-fluid bag in continuous ambulatory peritoneal dialysis (CAPD) or the like is carried out, it is necessary to connect tubes under a sterilized condition. For example, in JPB 61-30582, a tube connecting apparatus equipped with a pair of holders capable of holding two tubes to be connected in parallel and a cutting plate (plate-shaped heater element, wafer) capable of moving across the tubes which are placed between both of the holders is disclosed. In this tube connecting apparatus, the cutting plate is heated and moved to melt and cut the tubes in a state that the two tubes are held in parallel and in an opposite direction in grooves which are formed at the holders, then, one of the holders is moved in a diameter direction (row direction) of the tubes to coincide cut ends of the tubes to be connected each other, and the cutting plate is extracted by moving it to an evacuated position to fuse both of the tubes.

Further, for example, in JPA 6-91010, a tube connecting apparatus which employs the same tube connecting method as the above apparatus, which has a first clamp and a second clamp which hold two tubes in a parallel state, and which moves the first clamp in parallel to the second clamp, in order to improve reliability of tube connecting, is disclosed. The tube connecting apparatus has a first clamp movement mechanism that carries out merely forward or backward movement for advancing or retracting the first clamp, and a second clamp movement mechanism that moves the second clamp merely in a direction that the second clamp approaches/separates to/from the first clamp.

Furthermore, for example, in JPA 4-308731, a tube connecting apparatus, which employs the same principle of heating, melting and then connecting the tubes each other under a sterilized condition by utilizing a cutting plate, yet which connects the tubes in a state that liquid in the tubes is kept contained without leaking the liquid even in a case that the liquid remains inside the tubes before the tubes are cut, is disclosed. In this tube connecting apparatus, two tubes (a first tube, a second tube) are held on the same rotation locus respectively according to a pair of tube holders allowed to rotate relatively, after the two tubes are cut between the holders by a heated cutting plate, the tube holders are rotated such that a cut end face of one end side of the first tube aligns (corresponds to) a cut end face of another side of the second tube, and the cutting plate is evacuated to fuse both of the tubes. Moreover, for example, in JPA 9-154920, a tube connecting apparatus which is capable of not only connecting tubes in a state that liquid inside the tubes is kept contained and sealed without leaking the liquid but which can realize downsizing of the apparatus and of parts for the apparatus due to a small moving amount of the tubes at the time of connecting the tubes, is disclosed. In this tube connecting apparatus, two tubes to be connected are accommodated and held in two tube-holding assembly (a first tube-holding assembly, a second tube-holding assembly) in a contacted state with each other, after the two tubes are cut by a heated cutting plate, the second tube-holding assembly is rotated by 180 degrees relatively to the first tube-holding assembly such that cut end faces of the tubes are replaced with each other for alignment, and the cutting plate is evacuated to fuse both of the tubes.

In each of these conventional apparatuses, a cutting member for cutting the tubes in a heated state is usually used by changing it every time in a manner that it is disposed of at every connecting operation of the tubes. There are manual exchanging operation and automatic exchanging operation. In general, comparing with the manual exchanging operation, the automatic exchanging operation lowers workload for an operator and enhances working efficiency. As an example of the automatic exchanging operation, for example, JPA 2000-308670 (pages 8 to 9, FIGS. 1 and 2) discloses a tube connecting apparatus equipped with an automatic cutting member conveying mechanism which pushes cutting members accommodated in a cassette one by one to a conveying path to supply a cutting member to a predetermined position.

SUMMARY OF THE INVENTION

Problem to be solved by the Invention

However, in the conventional tube connecting apparatuses, when the apparatuses stop their operation due to interruption (shut off) or the like of power supply, since a special consideration for reset operation to the apparatus thereafter was not paid, there was a case that repair becomes necessary because the apparatuses have trouble due to that an operator forcibly takes off the tubes adhered to the cutting member from the apparatuses which stopped during connecting operation; there was a case that the apparatuses have trouble due to that blood in the tubes is scattered into an interior of the apparatuses; or there was a hazard that the scattered blood infects an operator. For these reasons, it is preferable that an operator can safely carry out reset operation without giving damage to the apparatus even in a case that the apparatus stops its operation due to interruption or the like of power supply.

In view of the above circumstances, an object of the present invention is to provide a tube connecting apparatus that can carry out self reset operation without giving damage to the apparatus and that safety of an operator is considered.

Means for solving the Problem

In order to achieve the above object, a first aspect of the present invention is directed to a tube connecting apparatus, comprising: a holding section which holds at least two flexible tubes to press them to a flat state; a cutting section which cuts the tubes held in a flat state by the holding section; an electrode section for supplying electric power for heating to the cutting section; a cutting section movement unit which moves the cutting section between a tube cutting position and a tube non-cutting position; a cutting section detecting sensor which detects the cutting section moved by the cutting section movement unit; a holding section movement unit which moves the holding section to change relatively positions of the cut tubes such that end portions to be connected contact closely each other; and a controlling section which controls power supply to the electrode section as well as movement of the cutting section movement unit and the holding section movement Unit, wherein, when the apparatus operates again after a halt, the controlling section judges necessity of reset operation in accordance with detecting information of the cutting section detected by the cutting section detecting sensor.

In the first aspect, at least two flexible tubes are held and pressed to a flat state by the holding section. Through the electrode section, electric power for heating is supplied to the cutting section which cuts the tubes held in a flat state by the holding section, the cutting section is moved from a tube non-cutting position to a tube cutting position by the cutting section movement unit, then the tubes held in a flat state by the holding section are cut. The holding section is moved to change positions of the at least two tubes cut by the cutting section relatively by the holding section movement unit such that end portions to be connected contact closely each other, thereby the tubes are connected with each other. Power supply to the electrode section as well as movement of the cutting section movement unit and the holding section movement unit are controlled by the controlling section. When the apparatus operates again after a halt, the controlling section judges necessity of reset operation in accordance with detecting information detected by the cutting section detecting sensor on the cutting section which is moved by the cutting section movement unit. According to the first embodiment, since the controlling section, when the apparatus operates again after a halt, judges necessity of reset operation in accordance with detecting information of the cutting section detecting sensor and controls the power supply to the electrode section as well as the movement of the cutting section movement unit and the holding section movement unit in a case that reset operation is necessary, self reset operation becomes practicable without giving damage to the tube connecting apparatus.

In this aspect, there are various embodiments for controlling of reset operation executed by the controlling section: For example, the controlling section may have a non-volatile memory which memorizes connecting process information expressing a state of connecting process of the tubes, and when the connecting process information memorized in the non-volatile memory is information expressing being in a state of connecting operation and when the cutting section detecting sensor detects the cutting section moved to the tube cutting position, the controlling section may judge that the reset operation is necessary and control the power supply to the electrode section as well as the movement of the cutting section movement unit and the holding section movement unit to carry out the reset operation. The apparatus may further comprises an engagement section which engages at least a part of the holding section to prohibit the holding section from opening movement out of the pressing state of the tubes; and a holding section lock sensor which detects an engagement state of the engagement section against the holding section, and when the connecting process information memorized in the non-volatile memory is information expressing being in a state of connecting operation and when the cutting section detecting sensor detects the cutting section moved to the tube cutting position and the holding section lock sensor detects the holding section engaged with the engagement section, the controlling section may judge that the reset operation is necessary and control the power supply to the electrode section as well as the movement of the cutting section movement unit and the holding section movement unit to carry out the reset operation. The apparatus may further comprises an engagement section which engages at least a part of the holding section to prohibit the holding section from opening movement out of the pressing state of the tubes; and a display section for displaying information, and when the controlling section judges that the reset operation is necessary, the controlling section may control the power supply to the electrode section as well as reset operation of the cutting section movement unit, the holding section movement unit and the engagement section, and control the display section to display error indication.

In such a embodiment, when a predetermined time lapsed from beginning of heating of the electrode section to the cutting section, the controlling section may drive the non-volatile memory to memorize the information expressing being in a state of connecting operation as the connecting process information. The apparatus may further comprises a position detecting sensor which detects that the holding section moved by the holding section movement unit reached a connection finish position for contacting closely the end portions of the cut tubes each other, and when the position detecting sensor detects that the holding section reached the connection finish position, the controlling section may drive the non-volatile memory to memorize information expressing being in a state of non-connecting operation as the connecting process information. Further, the cutting section may have a cutting plate which cuts the tubes, and the non-volatile memory is capable of memorizing exchange information of the cutting plate, and the apparatus may further comprises a cutting plate conveying section which conveys the cutting plate to the cutting section replaceably, and when the connecting process information memorized in the non-volatile memory is information expressing being in a state of non-connecting operation and when the exchange information memorized in the non-volatile memory is information expressing being unexchanged, the controlling section may control the cutting plate conveying section to convey the cutting plate to the cutting section. At this time, the apparatus may further comprises a cutting plate conveying section detecting sensor which detects the cutting plate conveying section, and the cutting plate conveying section is movable so as to convey the cutting plate to the cutting section, and when the cutting plate conveying section detecting sensor detects the moved cutting plate conveying section, the controlling section may drive the non-volatile memory to memorize information expressing being exchanged as the exchange information of the cutting plate. The apparatus may further comprises: an engagement section which engages at least a part of the holding section to prohibit the holding section from opening movement out of the pressing state of the tubes; and a holding section lock sensor which detects an engagement state of the engagement section against the holding section, and the cutting section has a cutting plate which cuts the tubes, and the non-volatile memory is capable of memorizing exchange information of the cutting plate, and when the connecting process information memorized in the non-volatile memory is information expressing being in a state of non-connecting operation and when the holding section lock sensor detects the holding section engaged with the engagement section, the controlling section may drive the non-volatile memory to memorize information expressing being unexchanged as the exchange information of the cutting plate.

In the first aspect, when the engagement section is a self-holding type solenoid into which a permanent magnet and a plunger are accommodated, even if power supply is interrupted during connecting operation of the tubes, since touching to the cutting section by an operator is prohibited because the engagement section is self-held to keep a state of prohibiting the holding section from opening operation out of a pressing state of the tubes, safety can be secured.

Further, in order to achieve the above object, a second aspect of the present invention is directed to a tube connecting apparatus, comprising: a holding section which holds at least two flexible tubes to press them to a flat state; a cutting section which cuts the tubes held in a flat state by the holding section; an electrode section for supplying electric power for heating to the cutting section; a cutting section movement unit which moves the cutting section between a tube cutting position and a tube non-cutting position; a holding section movement unit which moves the holding section to change relatively positions of the cut tubes such that end portions to be connected contact closely each other; a controlling section which controls power supply to the electrode section as well as movement of the cutting section movement unit and the holding section movement unit; and a display section for displaying information, wherein the controlling section has a non-volatile memory which memorizes connecting process information expressing a state of connecting process of the tubes, and when the apparatus operates again after a halt, the controlling section judges necessity of reset operation in accordance with the connecting process information memorized in the non-volatile memory, and when the controlling section judges that the reset operation is necessary, the controlling section controls the display section to display error indication. According to the second aspect, since the controlling section, when the apparatus operates again after a halt, judges necessity of reset operation in accordance with the connecting process information memorized in the non-volatile memory, and controls the power supply to the electrode section as well as the movement of the cutting section movement unit and the holding section movement unit in a case that reset operation is necessary, self reset operation becomes practicable without giving damage to the tube connecting apparatus, and since the controlling section controls the display section to display error indication, the apparatus can draw an operator's attention to the tubes to be connected. In the second aspect, the apparatus may further comprises an engagement section which engages at least a part of the holding section to prohibit the holding section from opening movement out of the pressing state of the tubes, and when the connecting process information memorized in the non-volatile memory is information expressing being in a state of connecting operation, the controlling section may judge that the reset operation is necessary and control reset power supply to the electrode section as well as reset operation of the cutting section movement unit, the holding section movement unit and the engagement section.

Effects of the Invention

According to the present invention, since the controlling section, when the apparatus operates again after a halt, judges necessity of reset operation in accordance with detecting information of the cutting section detected by the cutting section detecting sensor or in accordance with the connecting process information memorized in the non-volatile memory, effects that self reset operation becomes practicable without giving damage to the tube connecting apparatus can be obtained.

BRIEF DESCRIPTION OF THE DRAWINGS

FIG. 23 is a side view showing evacuation movement of a tube-pushing member, FIG. 23(A) showing a state just before a tip portion of the tube-pushing member presses tubes to a flat state, FIG. 23(B) showing a state that the tip portion of the tube-pushing member presses the tubes to a flat state, and FIG. 23(C) showing a state that a wafer cuts the tubes held in a flat state;

FIG. 24 is a side view showing a state of evacuating the wafer from a cutting position by descending a holding member which holds the wafer;

With reference to embodiments below, the present invention will become more apparent.

DETAILED DESCRIPTION OF THE PREFERRED EMBODIMENTS

With reference to the drawings, embodiments of a tube connecting apparatus that cuts and then connects two tubes in which blood is contained and sealed and that the present invention is applied to will be explained.

(Structure)

Figure 1:
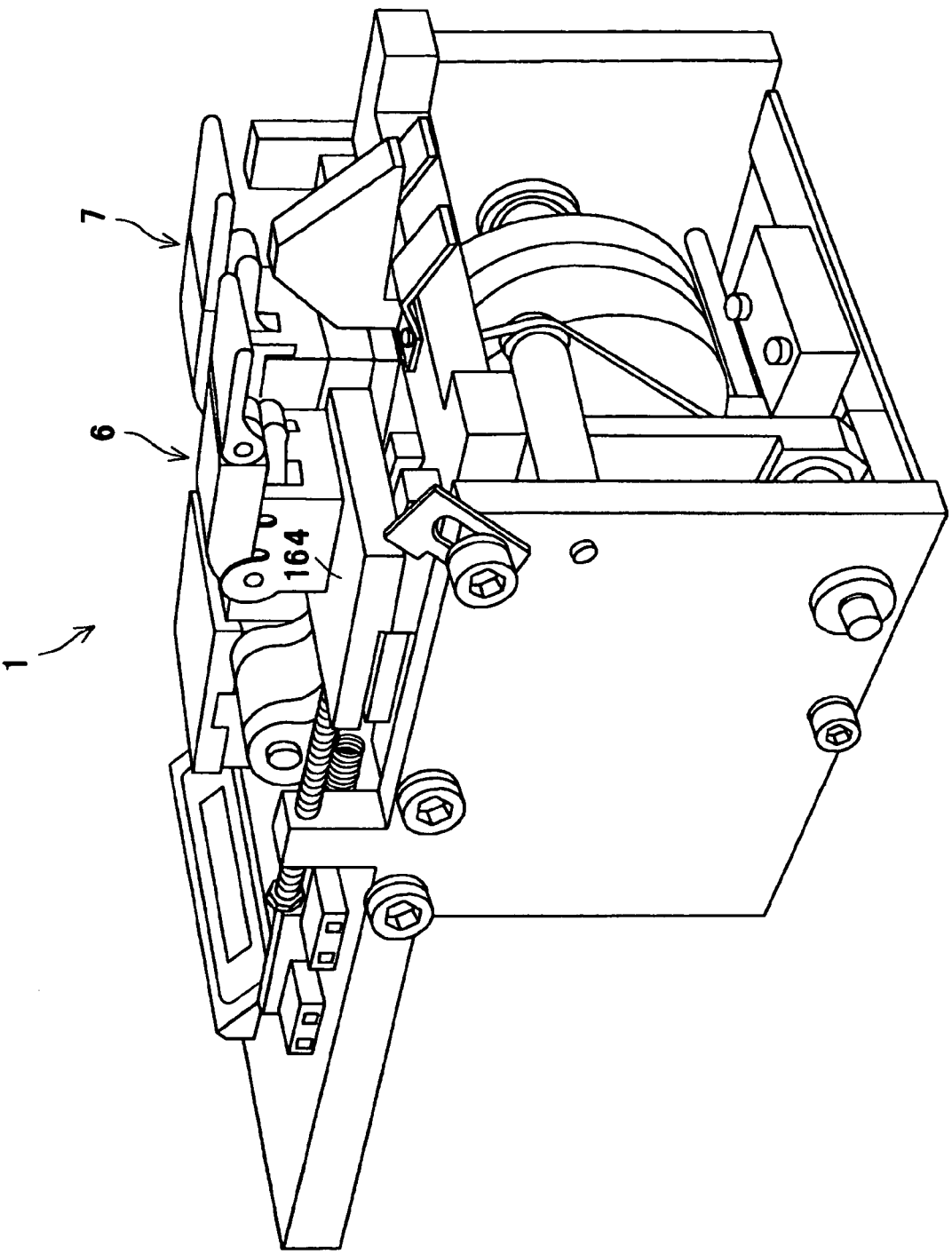
FIG. 1 is a schematic perspective view of a tube connecting apparatus in an embodiment to which the present invention is applicable.
Figure 2:
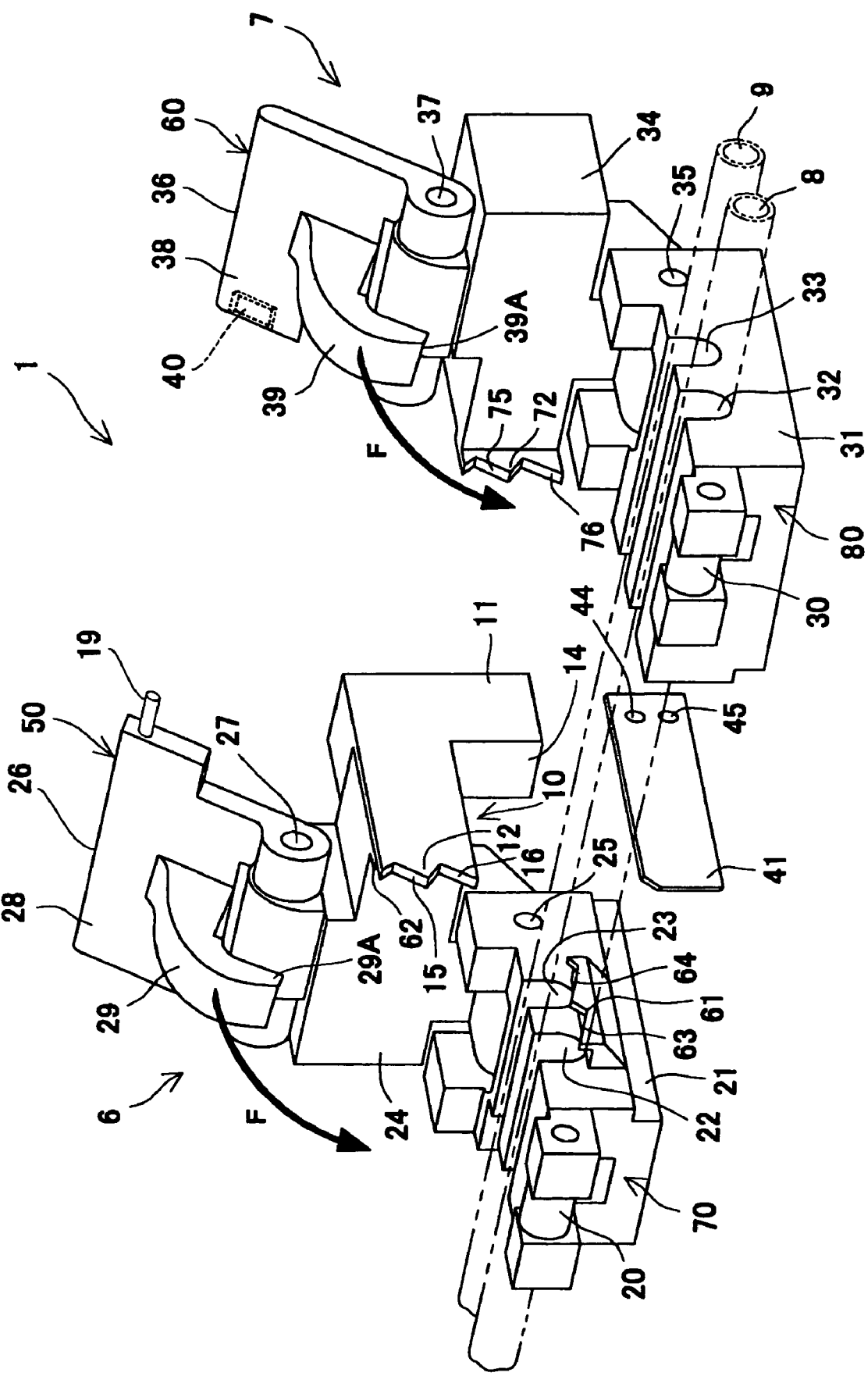
FIG. 2 is a perspective view showing clamps of the tube connecting apparatus.

As shown in FIGS. 1 and 2, a tube connecting apparatus 1 of the present embodiment is equipped with a first clamp 6 and a second clamp 7 serving as a holding section both of which hold two flexible tubes 8, 9 approximately in a parallel state, and a tube-pushing member 10 which is disposed between the first clamp 6 and second clamp 7 and adjacent to the first clamp 6 to press the tubes to a flat state. The tube connecting apparatus 1 is accommodated in a casing such that protruded members as shown in FIG. 1 are hidden. (See FIG. 3.)

The first clamp 6 has a first upper jaw portion 50 which forms an upper jaw of the first clamp 6 to press the tubes 8, 9 to a flat state, and a first lower jaw portion 70 which forms a lower jaw of the first clamp 6 to support the tubes 8, 9 pressed to a flat state by the first upper jaw portion 50. On the other hand, the second clamp 7 has a second upper jaw portion 60 which forms an upper jaw of the second clamp 7 to press the tubes 8, 9 to a flat state, and a second lower jaw portion 80 which forms a lower jaw of the second clamp 7 to support the tubes 8, 9 pressed to a flat state by the second upper jaw portion 60.

The tubes 8, 9 are made of soft resin such as, for example, soft polyvinyl chloride or the like and have flexibility, in which blood is contained and sealed. These tubes 8, 9 have approximately the same shape with respect to an inner diameter, an outer diameter and a length in a state before blood is contained and sealed. The first clamp 6 has a holder 21 for holding the tubes 8, 9, and a covering body 24 which is fitted pivotably to a rear end portion of the holder 21 through a hinge 25 for opening and closing.

A pair of grooves 22, 23 which are parallel with each other and into which the two tubes 8, 9 are put are formed in the holder 21. A cross-section of the grooves 22, 23 is shaped as a letter U. It is preferable that a width of the grooves 22, 23 is set to have the same or a smaller width as/than a diameter of the tubes 8, 9 in an in artificial state. An operator pushes the tubes 8, 9 into inner sides thereof (downward direction in FIG. 2) to put the tubes 8, 9 into the grooves 22, 23. The covering body 24, in a closed state, covers the grooves 22, 23 and has a function for fixing the tubes 8, 9 such that the tubes are put inside the grooves 22, 23 so as not to get rid of the grooves.

The first clamp 6 has an engagement mechanism 26 for retaining the covering body 24 in a closed state. The engagement mechanism 26 is constituted by a plate piece 28 which is fixed pivotably to a tip of the covering body 24 through a hinge 27, a pawl member 29 which is formed to protrude toward an inner face of the plate piece 28, and an engagement roller 20 which is provided pivotably at a front end of the holder 21. Accordingly, by pivoting the plate piece 28 in a direction of an arrow F in FIG. 2 to engage the pawl member 29 with the engagement roller 20 in a state that the covering body 24 is closed. Further, a shaft 19 which protrudes toward a side of the second clamp 7 from an end face of the plate piece 28 is fitted to the plate piece 28.

The tube-pushing member 10 is connected with the first clamp 6 at a side of the second clamp 7. The first clamp 6 has a saw-shaped pressure closing member 61 which is fixed to a side face of the holder 21, and a saw-shaped pressure closing member 62 which is fixed to a side face of the covering body 24 and which bites the pressure closing member 61 each other. The pressure closing member 61 has inclined faces 63, 64 at positions corresponding to the grooves 22, 23 respectively, while inclined faces 65, 66, which are parallel to the inclined faces 63, 64 respectively and which are disposed at positions having a predetermined distance from the inclined faces 63, 64, are formed at the pressure closing member 62. (See FIG. 24.) Accordingly, when the covering body 24 is closed in a state that the tubes 8, 9 are put in the grooves 22, 23, the tube 8 is pressed by the inclined faces 63, 65 and the tube 9 is pressed by the inclined faces 64, 66 since the pressure closing members 61, 62 bite each other. According to the structure of the first clamp 6, dislocation (offset) or deformation of the tubes 8, 9 is restrained and easy and proper connection is secured when cut faces of the tubes 8, 9 are connected with each other, which will be stated later.

On the other hand, the second clamp 7 is disposed at a side of the first clamp 6 and adjacent to the first clamp 6 via the tube-pushing member 10. The second clamp 7, in the same manner as the first clamp 6, has a holder 31 at which a pair of grooves 32, 33 are formed and which holds the tubes 8, 9, a covering body 34 which pivots to the holder 31 for opening and closing, and an engagement mechanism 36. A structure thereof corresponds to the first clamp 6: the engagement mechanism 36 has a hinge 37, a plate piece 38 and a pawl member 39 having a tip portion 39A; and the holder 31 has a hinge 35 and an engagement roller 30. Incidentally, a long hole 40 into which the shaft 19 can be inserted is formed at an end face of the plate piece 38 facing a side of the first clamp 6. The long hole 40 has a function for allowing the shaft 19 to move when the first clamp 6 moves in tube connecting operation as stated later.

The second clamp 7 is constituted to have a saw-shaped pressure closing member 71 (unillustrated) which is fixed to a side face of the holder 31 and at a side of the holder 21, and a saw-shaped pressure closing member 72 which is fixed to a side face of the covering body 34 and at a side of the covering body 24 and which bites the pressure closing member 71 each other. The pressure closing member 71 has inclined faces 73, 74 at positions corresponding to the grooves 32, 33, respectively (See FIG. 24.) Inclined faces 75, 76, which are parallel to the inclined faces 73, 74 respectively and which are disposed at positions having a predetermined distance from the inclined faces 73, 74, are formed at the pressure closing member 72.

The first clamp 6 and the second clamp 7 are usually located such that the grooves 22, 32 correspond to (align) the grooves 23, 33 respectively each other.

The tube-pushing member 10 is disposed movably and integrally with the first clamp 6. Further, the tube-pushing member 10 has a saw-shaped tip portion 12 (corresponding to the pressure closing members 62, 72) at which inclined faces 15, 16 are formed in the same manner as the first clamp 6 and the second clamp 7. However, it differs from the first clamp 6 and the second clamp 7 in that it does not have the pressure closing members 61, 71 which bite each other via the tubes 8, 9. Furthermore, the tip portion 12 of the tube-pushing member 10 is placed at a position protruded a little more than a position of the pressure closing member 62 of the first clamp 6, although the tip portion 12 has the same saw shape as the pressure closing member 62 of the first clamp 6 and the pressure closing member 72 of the second clamp 7.

A supporting member 11 having a L shaped cross section is fixed to the tube-pushing member 10 by screws. The supporting member 11 has a supporting member projection portion 14 which projects downward. An unillustrated U shaped slider is provided at the supporting member 11. This slider is allowed to move along an unillustrated rail. The unillustrated rail is fixed to a rail supporting member (unillustrated) and the rail supporting member is fixed to the covering body 24 by screws. For this reason, the tube-pushing member 10 is integrated with the first clamp 6 and can move relatively to the first clamp 6. Incidentally, since the tip portion 12 of the tube-pushing member 10 is protruded more than the pressure closing member 62 of the first clamp 6, the tip portion 12 pushes the tubes 8, 9 prior to the first clamp 6 when the covering body 24 is closed.

Figure 3:
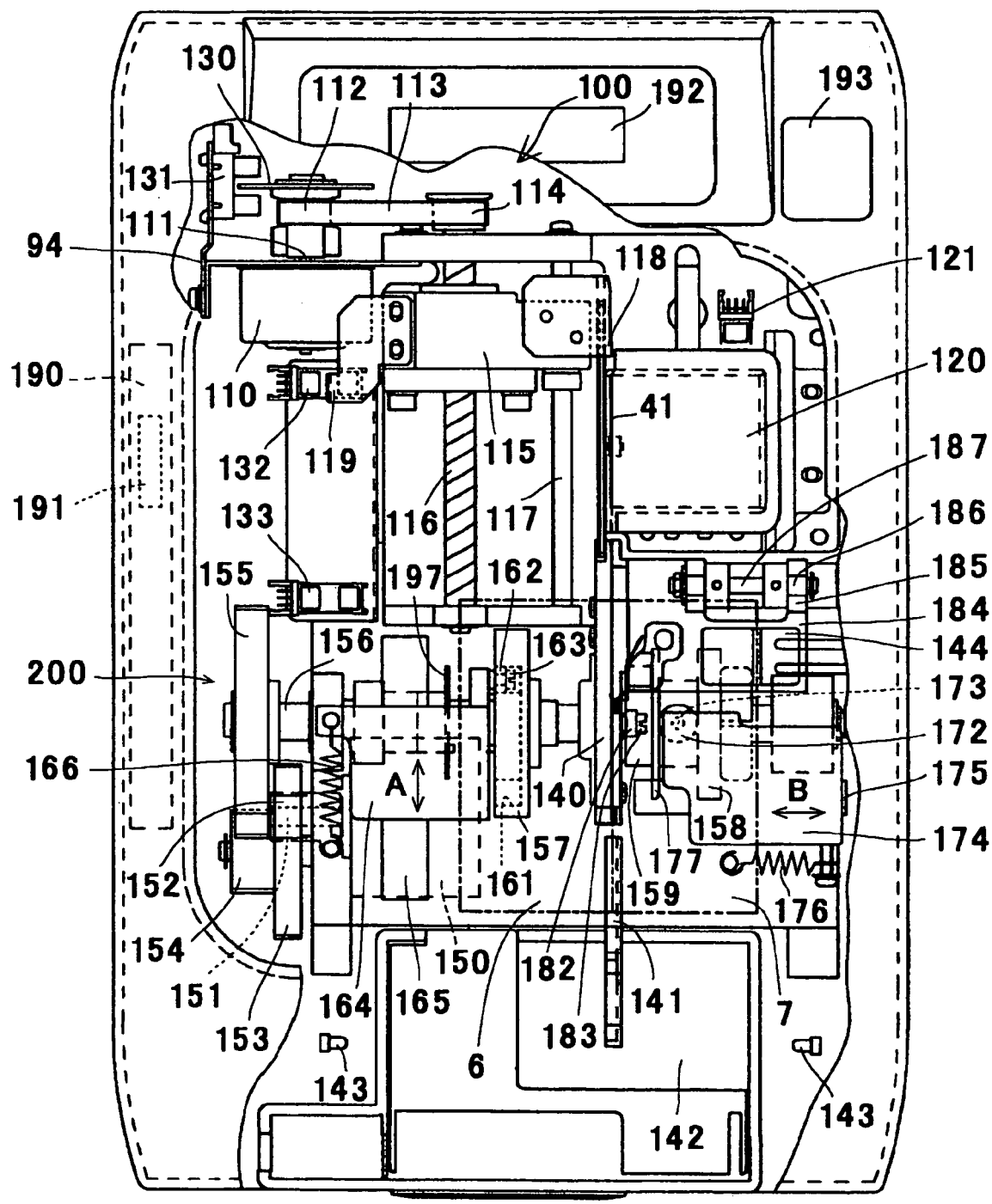
FIG. 3 is a partially broken plan view of the tube connecting apparatus.

Further, as shown in FIG. 3, the tube connecting apparatus 1 is equipped with a wafer feeding mechanism 100 (a cutting plate conveying section) which feeds the wafer serving as a cutting plate.

A fitting member 94 is set up at the casing of the tube connecting apparatus 1 and a wafer feeding motor 110 which is made of a pulse motor capable of normal and reverse rotation is fixed by screws to the fitting member 94. A gear 112 is fixed to an output shaft 111 of the wafer feeding motor 110, and a timing belt 113 is entrained between the gear 112 and a gear 114. The gear 114 is disposed at an axis of a ball screw 116 on which a wafer feeding member 115 that feeds the wafer 41 capable of cutting the tubes 8, 9 one by one is provided and that is called as a shuttle. An unillustrated nut which engages the ball screw 116 is provided at an interior of the wafer feeding member 115. The wafer feeding member 115 moves along the ball screw 116 due to rotation of the ball screw 116 in accordance with rotation of the gear 114 of which driving source is the wafer feeding motor 110. One side of the wafer feeding member 115 is supported by a rod-shaped shaft 117 to stabilize posture (movement) of the wafer feeding member 115 at the time of feeding the wafer. A feeding piece 118 which feeds the wafer 41 accommodated in a wafer cassette 120 which accommodates a plurality of wafers 41 (70 pieces in this embodiment) one by one from the wafer cassette 120 in accordance with movement of the wafer feeding member 115 is fixed at an end portion of the wafer feeding member 115. A wafer cassette detecting sensor 121 for detecting that the wafer cassette 120 is mounted is fixed at one side of the wafer cassette 120.

Unillustrated compression springs are disposed at an interior of the wafer cassette 120 so as to energize the wafers 41. When the wafer 41 is fed by the feeding piece 118 of the wafer feeding member 115, an adjacent wafer faces a side of the wafer feeding member 115 one after another, which allows the feeding piece 118 to feed the wafer 41 continuously. Incidentally, the wafer feeding member 115 can move in a direction opposite to a direction of feeding the wafer 41 according to reverse rotation of the wafer feeding motor 110.

The wafer 41 is a self-heating typed heat cutting plate. For example, a sheet of a metal plate such as a copper plate or the like is folded into two, and a resistance body having a desired pattern for heating is formed inside the folded metal plate via insulating layers to manufacture the wafer. The wafer 41 has a structure that terminals 44, 45 (See FIG. 2.) disposed at both ends of the resistance body are exposed at apertures formed at each end portion of the metal plate.

Further, a revolving plate 130 which is adjacent to the gear 112 and which has a plurality of slits and which rotates according to rotation of the wafer feeding motor 110 is fixed to an end portion of the output shaft 111 of the wafer feeding motor 110. The revolving plate 130 is provided to detect a moving amount of the wafer feeding member 115. At the vicinity of the revolving plate 130, a transmission type sensor 131 which detects a revolving amount of the revolving plate 130 is fixed by screws to the fitting member 94 at an opposite side of the gear 114 so as to stride the revolving plate 130.

A transmission type sensor 132 which detects the wafer feeding member 115 located at a feeding start position of the wafer 41 and which serves as a cutting plate conveying section detecting sensor, and a transmission type sensor 133 which detects the wafer feeding member 115 located at a feeding end position of the wafer 41 which serves as a cutting plate conveying section detecting sensor are disposed separately with a predetermined interval at an opposite side of the wafer cassette 120 via the ball screw 116. A piece to be detected 119 having an approximately L shape is fixed to the wafer feeding member 115 at an opposite side of the feeding piece 118. Incidentally, detection of the moving amount of the wafer feeding member 115 according to the above stated revolving plate 130 and the transmission type sensor 131 is carried out at an interval between both positions of the transmission type sensors 132, 133.

Figure 4:
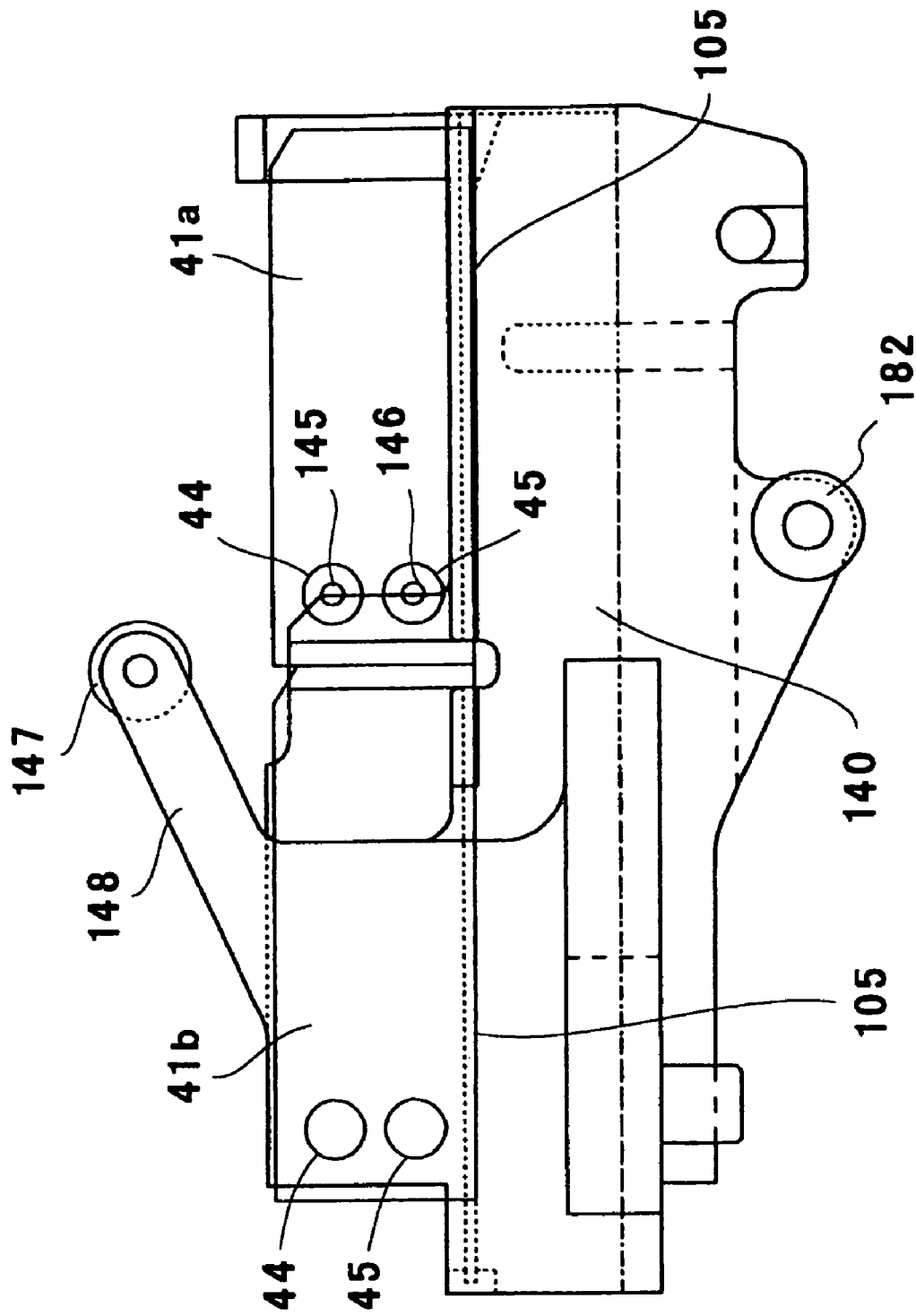
FIG. 4 is an enlarged side view of a wafer holder.

The wafer 41 fed by the wafer feeding member 115 is located to a downstream side of a wafer conveying path from the wafer cassette 120, then located inside the wafer holder 140 which holds the wafer 41. As shown in FIG. 4, in this embodiment, a structure that two pieces of the wafer 41 are held in the wafer holder 140 such that end faces thereof contact each other is employed, and the wafer 41 is supplied in a manner that a wafer 41a fed formerly from the wafer cassette 120 is pushed and moved on a conveying path 105 in the wafer holder 140 by a wafer 41b fed newly from the wafer cassette 120. In other words, the wafer 41b pushes and advances the wafer 41a forward, and the wafer 41a is located at a position for cutting the tubes 8, 9 in the wafer holder 140.

The terminals 44, 45 for the wafer 41a which is located at a forward side in the wafer holder 140 are supplied with electric power for heating the wafer 41a by projection-shaped electrode portions 145, 146 from an unillustrated power unit via a harness of which illustration is omitted. The electrode portions 145, 146 are fixed integrally to the wafer holder 140 and are disposed so as to face via the wafer 41 to an end surface of one wall side (a back side in FIG. 4) of the wafer holder 140. Incidentally, as stated later, because the wafer holder 140 moves up and down at the time of cutting the tubes 8, 9, the electrode portions 145, 146 integrally fixed to the wafer holder 140 also have a structure capable of supplying electric power for heating to the wafer 41.

The resistance body inside the wafer 41 generates heat according to electricity supply from the electrode portions 145, 146, and the wafer 41 is heated up to the temperature (ex. approximately 260 to 320 deg. C.) capable of melting and cutting the tubes 8, 9. Further, because it is preferable that the wafer 41 is disposable (for single use) at every connecting operation of the tubes, the wafer feeding mechanism 100 has a structure capable of exchanging the wafer 41 held in the wafer holder 140 every time the tubes 8, 9 are connected.

The wafer holder 140 is heated by a heater 144 which is fitted to a pivot-supporting plate 184 which will be stated later. (See FIG. 3.) While electric power is supplied to the heater 144 from the unillustrated power unit, the wafer holder 140 always keeps a heated state during a period that electric power is supplied to the tube connecting apparatus 1. A holder temperature sensor 508 (See FIG. 13.) such as a thermistor or the like which detects a temperature of the wafer holder 140 is fixed to the wafer holder 140, and the wafer holder 140 is controlled to keep a predetermined temperature (70 deg. C. in this embodiment).

Temperature controlling in this embodiment will be explained further. Since a surface of the wafer 41 is covered by the copper plate as stated above, the wafer 41 is influenced by the temperature that the wafer holder 140 has due to the material (copper) characteristics when it is inserted into the wafer holder 140 and it reaches the predetermined temperature immediately after it is inserted into the wafer holder 140. A controlling unit 190 as stated later forecasts that the wafer 41 supplied electric power from the electrode portions 145, 146 reaches a predetermined temperature (ex. about 260 to 320 deg. C. as stated above) after a predetermined period of time from a time that the wafer 41 is inserted into the wafer holder 140 in order to shift to tube-cutting operation according to the wafer 41 (ascending movement of the wafer holder 140).

Figure 5:
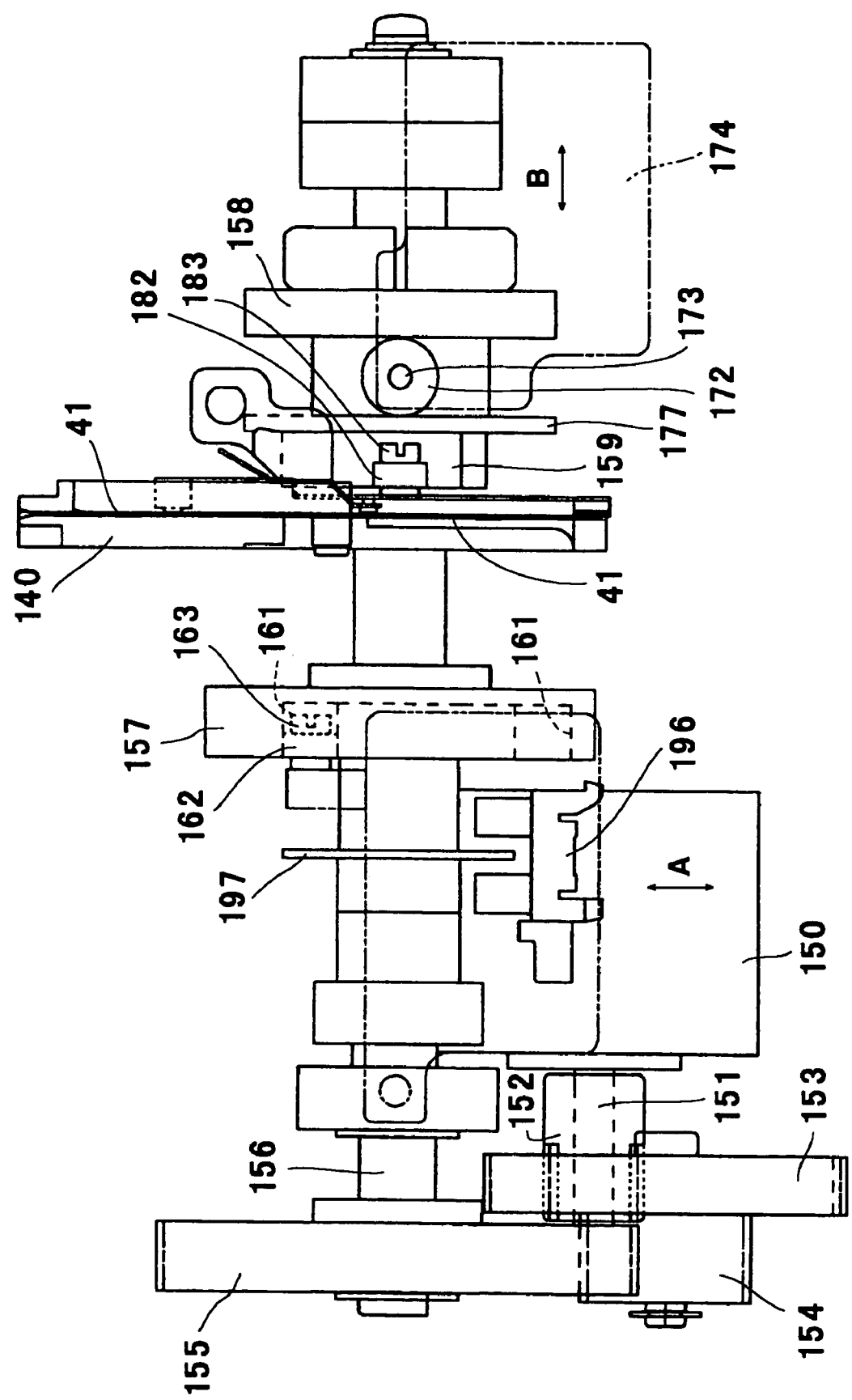
FIG. 5 is an enlarged side view of a drive-conveying mechanism.

As shown in FIGS. 3 and 5, the tube connecting apparatus 1 is equipped with a drive-conveying mechanism 200 which moves the first clamp 6 and the second clamp 7 and which functions as a holding section movement unit, and which moves the wafer holder 140 (up and down) and which functions as a cutting section movement unit.

A cam motor 150 which is a driving source of the drive-conveying mechanism 200 and which is made of a pulse motor capable of normal and reverse rotation is fitted by screws to an unillustrated motor fitting member which is fixed to the casing of the tube connecting apparatus 1 at a side of the wafer holder 140 and at a downstream side of the wafer feeding member 115. A gear 152 is fixed to an output shaft 151 of the cam motor 150 and the gear 152 bites a gear 153 each other. A gear 154 is fixed on a coaxial line of the gear 153 and this gear 154 bites a gear 155 each other. A driving shaft 156 which rotates together with the gear 155 according to driving force conveyed to the gear 155 is provided at a center of rotation for the gear 155. A cam 157 which regulates movement of the first clamp 6, a cam 158 which regulates movement of the second clamp 7 and a cam 159 which regulates movement of the wafer holder 140 are respectively fixed on the driving shaft 156. Accordingly, driving force from the cam motor 150 is conveyed to the driving shaft 156 and the cams 157, 158 and 159 are driven to rotate respectively.

A groove 161 is formed at an interior of the cam 157, and a bearing 162 which engages an edge face of the groove 161 is connected via a fitting member 163 to a supporting table 164 (See FIG. 1.) which supports the first clamp 6 in a fixed state. For this reason, the bearing 162 slides along the edge face of the groove 161 formed at the interior of the cam 157 to enable the first clamp 6 to move in a predetermined direction (a direction of an arrow A in FIG. 3). Incidentally, a liner guide 165 which guides the supporting table 164 (the first clamp 6) so as to move stably is disposed at a bottom portion of the supporting table 164 in a contact state. Further, a compression spring 166 is bridged at one end of the supporting table 164 so as to energize this supporting table 164 to a predetermined direction.

On the other hand, a bearing 172 which engages a surface of the cam 158 is connected via a fitting member 173 to a supporting table 174 which supports the second clamp 7 in a fixed state. For this reason, according to rotation of the cam 158, the bearing 172 slides along the surface of the cam 158 to enable the second clamp 7 to move in a predetermined direction (a direction of an arrow B in FIG. 3). Incidentally, in this embodiment, the bearing 172 is constituted to not only engage a side face of the cam 158 but also engage a surface of a flange portion 177 which is integrally formed with the cam 159 which regulates the movement of the wafer holder 140. In short, the bearing 172 is located between the side face of the cam 158 and the flange portion 177 so that the bearing 172 has a structure capable of engaging and sliding on both of them, and the flange portion 177 is included in a part of a function of the cam 158 which regulates the movement of the second clamp 7. A notched portion 178 (See FIGS. 25(C) and (D).) is formed at a part of the cam 158 as stated later. Incidentally, a liner guide 175 which guides the supporting table 174 (the second clamp 7) so as to move stably is disposed at a bottom portion of the supporting table 174 in a contact state. Further, a compression spring 176 is bridged at one end of the supporting table 174 so as to energize this supporting table 174 to a predetermined direction.

Further, a bearing 182 (See FIG. 4.) is fitted via a fitting member 183 to a bottom portion of the wafer holder 140. Because the bearing 182 slides along a surface shape of the cam 159 according to rotation of the cam 159, the wafer holder 140 is constituted so as to move in a predetermined direction (a vertical direction). In other words, by pivoting integrally with and around a shaft axis 187 which penetrates a hole 186 formed at a protruded portion 185 of the pivot-supporting plate 184 which is fitted to the wafer holder 140, the wafer holder 140 is structured so as to be able to swing in a vertical direction. A slanted projection portion 148 which has a metal roller 147 at its tip is integrally formed with an upper side of the wafer holder 140 (See FIG. 4.), and the roller 147 is brought to contact the supporting member projection portion 14 (See FIG. 2.). Due to a change in the surface shape of the cam 159, when the wafer holder 140 ascends (swings) at a predetermined timing, the tube-pushing member 10 (See FIG. 2.) is pushed upward. Thus, the projection portion 148 has a function for guiding the tube-pushing member 10 to the evacuating position.

Figure 6:
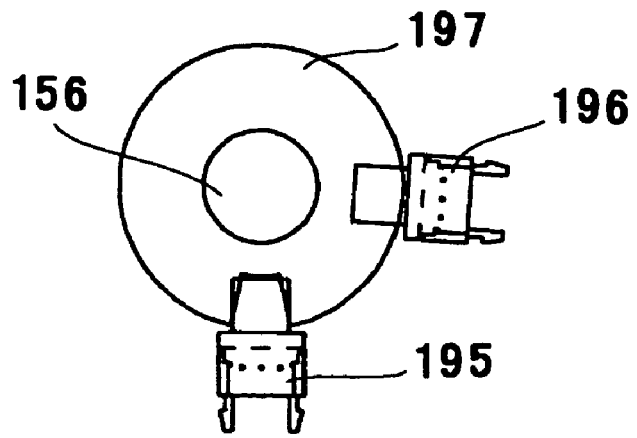
FIG. 6 is a side view showing a revolving plate fitted to a driving shaft and transmission type sensors.
Figure 6:
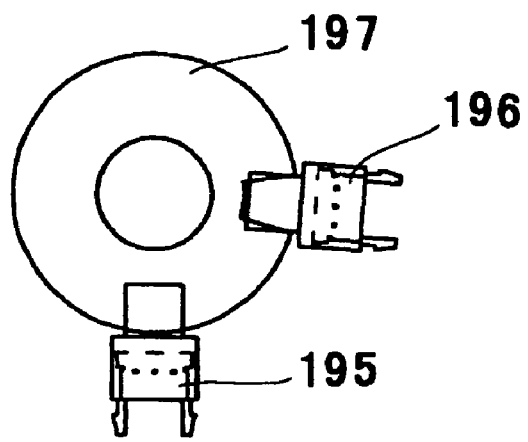
Figure 6:
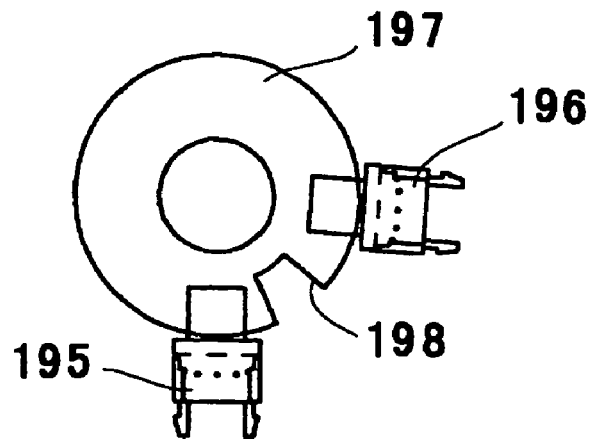

Further, a revolving plate 197 at which a notch 198 is formed is fixed to the driving shaft 156 between the cam 157 and the gear 155. (See FIG. 6.) Transmission type sensors 195, 196, each serving as a position detecting sensor, are disposed adjacent to the revolving plate 197 so as to stride the revolving plate 197. By utilizing the notch 198 formed at the revolving plate 197, position detection for the first clamp 6 and the second clamp 7 is carried out by the transmission type sensors 195 and 196. Namely, while the revolving plate 197 rotates in a predetermined direction according to rotation of the driving shaft 156, when light from the transmission type sensor 195 transmits the notch 198 (See FIG. 6(A).), the first clamp 6 and the second clamp 7 are defined at their initial positions. Namely, the transmission type sensor 195 is used as a sensor for detecting the initial positions of the first clamp 6 and the second clamp 7. Further, the transmission type sensor 196 is used as a sensor for detecting that connection operation of the tubes 8, 9 is finished, and the notched portion 198 is located at a position facing the transmission type sensor 196 when connecting operation is finished. (See FIG. 6(B).)

As shown in FIG. 3, a guide 141 which guides (constitutes the conveying path for) a used wafer 41 and a waste box 142 which accommodates the used wafer(s) 41 are disposed at a downstream side of the wafer holder 140. The wafer 41 located at a position at which it can cut the tubes is wasted (accommodated) to the waste box 142 after cutting and connecting operation of the tubes 8, 9 is carried out. This wasting operation is also carried out by pushing the end faces of the wafers 41 each other as stated above. The wasted wafer 41 is guided along the guide 141 and then dropped into the waste box 142 to accommodate it. A transmission type wafer full state sensor 143 at which a light emitting element and a light receiving element are disposed separately and which detects a full state of the used wafers 41 wasted and accommodated in the waste box 142 is disposed at a side of the waste box 142 and at a position having a predetermined height from a bottom of the waste box 142.

Figure 7:
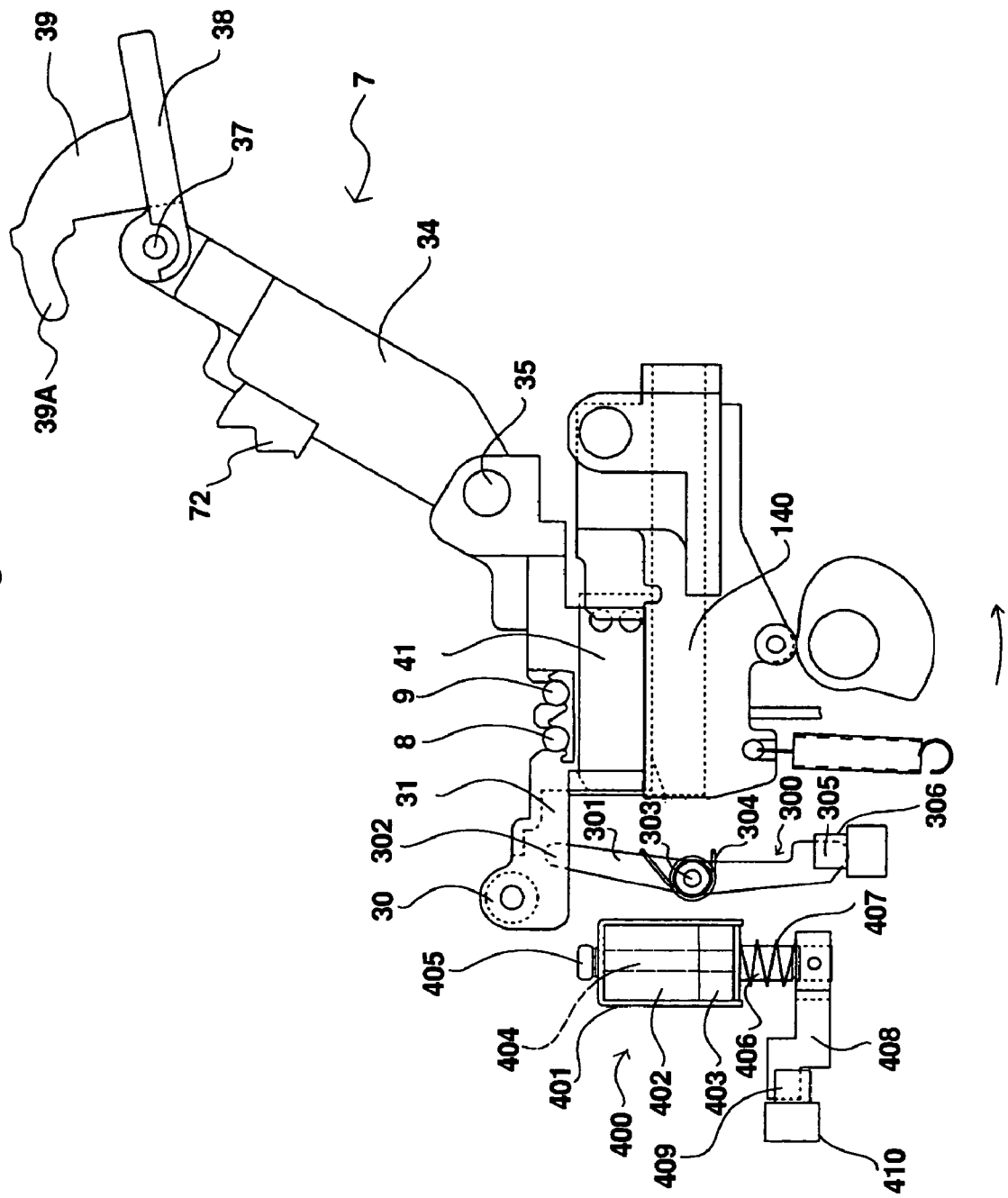
FIG. 7 is a right side view showing a state that a second clamp is opened.
Figure 8:
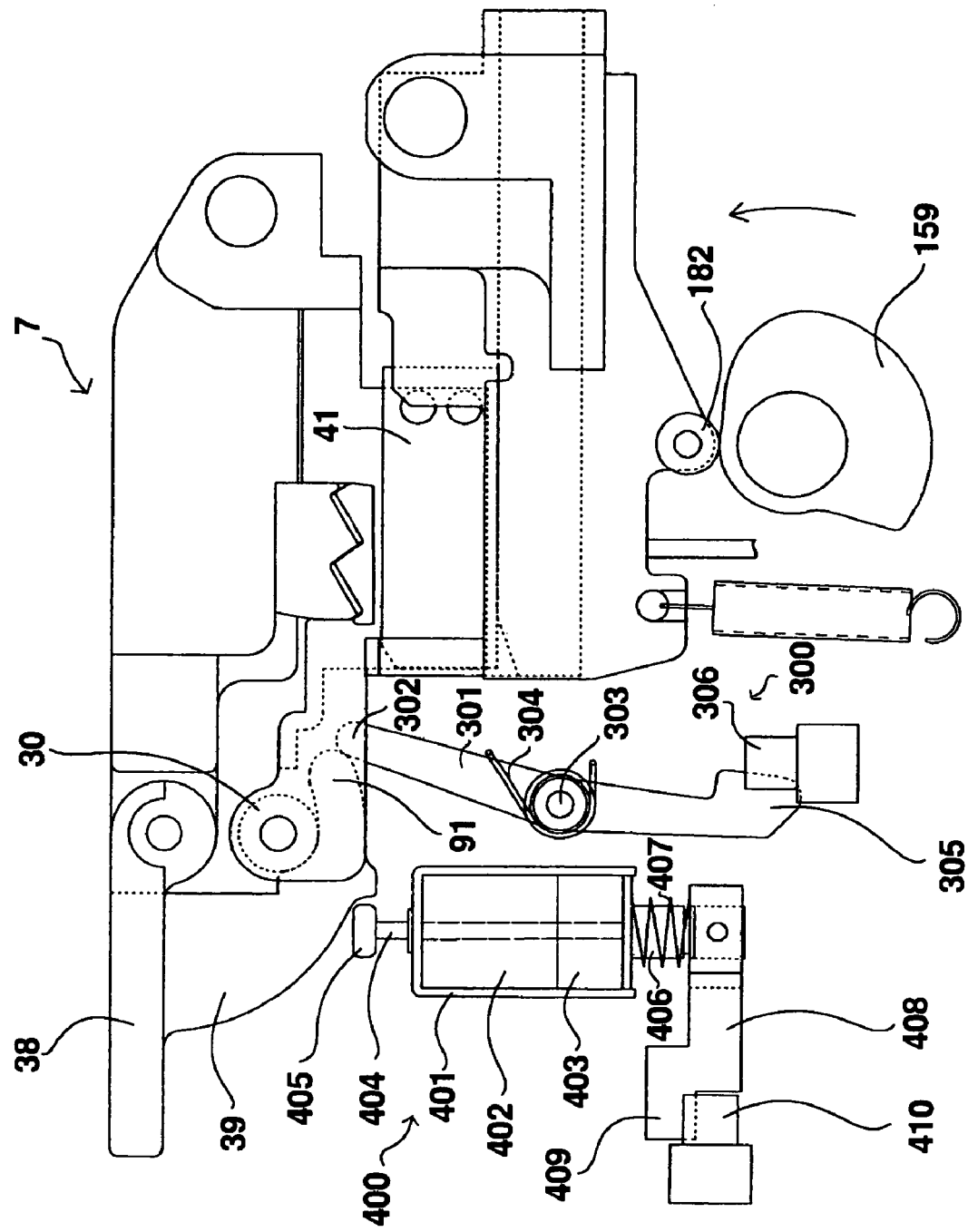
FIG. 8 is a right side view showing a state that the second clamp is closed and a wafer is located at a non-cutting position.
Figure 9:
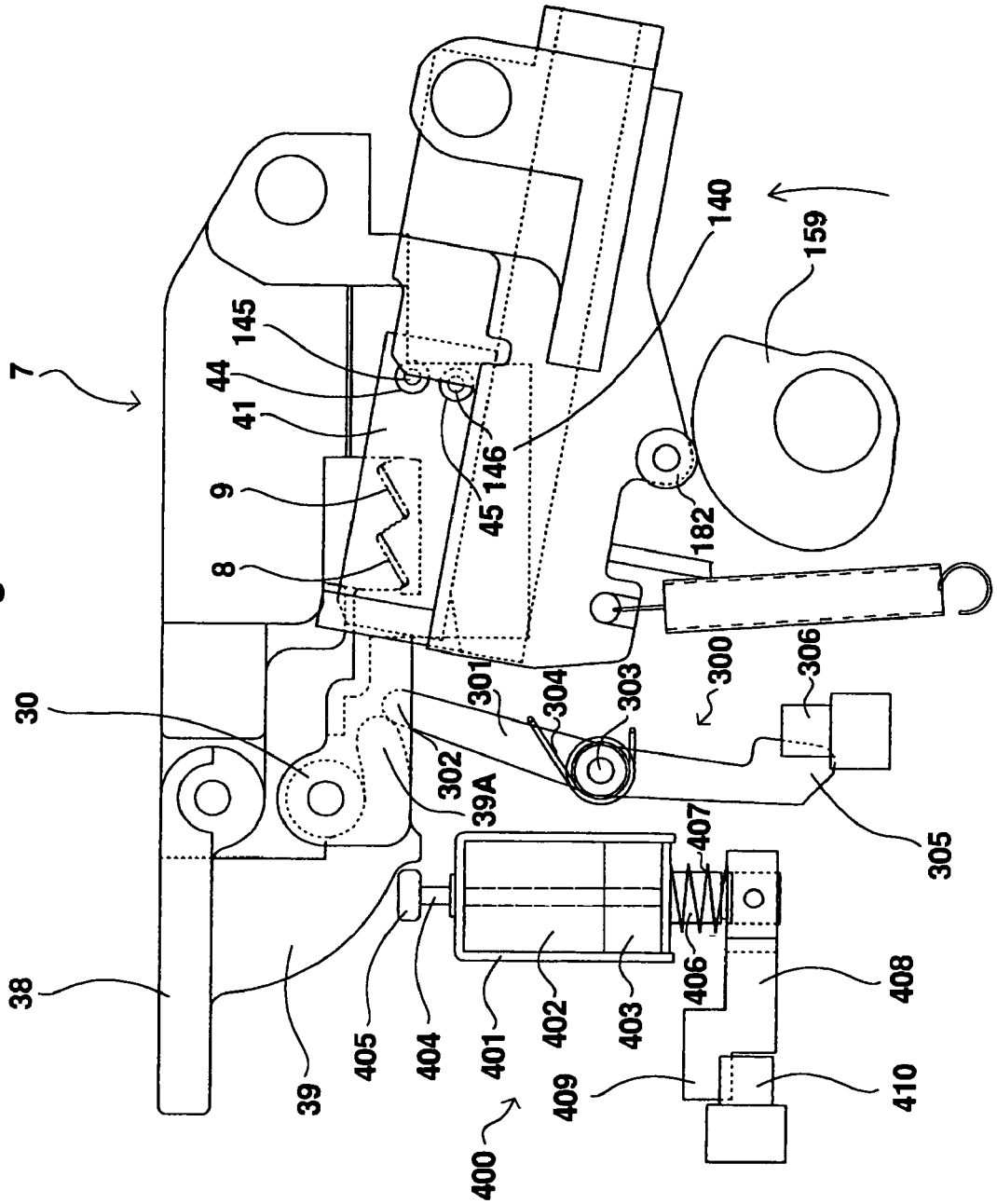
FIG. 9 is a right side view showing a state that the second clamp is closed and the wafer is located at a cutting position.

As shown in FIGS. 7 to 9, a clamp lock solenoid 400, which serves as an engagement section and which locks the covering body 34 so as not to open by engaging the tip portion 39A of the pawl member 39 in the second clamp 7 with the engagement roller 30 (which prohibits the tubes 8, 9 from release movement out of a pressing state), is disposed at a side opposing to the second lower jaw portion 80 of the second clamp 7 located at a right side of the tube connecting apparatus 1 and is disposed at a downward of the engagement roller 30. For this reason, difficulties in cutting and connecting of the tubes are prevented since the covering body 34 is prevented from being opened unexpectedly during connecting of the tubes, and accordingly fixing (holding) to the tubes 8, 9 as well as pressing according to the second clamp 7 are not canceled. Incidentally, since the shaft 19 of the first clamp 6 is inserted into the long hole 40 of the second clamp 7 such that the first clamp 6 and the second clamp 7 are constituted to move integrally in a linking manner, a locking function due to the clamp lock solenoid 400 acts not only on the second clamp 7 but also on the first clamp 6.

A general self-holding type solenoid is used for the clamp lock solenoid 400. Namely, the clamp lock solenoid 400 has an electromagnet 402 having an unillustrated coil and a permanent magnet 403 in a fixed frame 401. A plunger 404, which is movable in a direction of projecting out of the frame 401 so as to stop the pawl member 39 in a locking state (a state of projecting upward as shown in FIGS. 8 and 9) and in a direction of going back to the frame 401 so as to release the pawl member 39 from the locking state to allow the covering body 34 to open (a state of pulling downward as shown in FIG. 7), is inserted into the electromagnet 402 and the permanent magnet 403. An expanded diameter portion 405 whose diameter is expanded larger is formed at a tip portion of the plunger 404 (an upper side shown in FIGS. 7 to 9). When the unillustrated coil of the electromagnet 402 is charged with electricity (When the solenoid is magnetized), the expanded diameter portion 405 projecting out of the frame 401 engages (abuts against) the pawl member 39 such that opening movement of the pawl member 39 is prohibited. (See FIGS. 8, 9.)

Further, even if electricity to the unillustrated coil is stopped (the solenoid is demagnetized) in a state that the plunger 404 projects (moves up) out of the frame 401, the expanded diameter portion 405 is kept located at a projecting position because the permanent magnet 403 holds the plunger 404. Incidentally, as stated later, when power supply to the tube connecting apparatus 1 is cut off during connecting of the tubes 8, 9, the expanded diameter portion 405 maintains its projecting state because a position of the plunger 404 is retained by an effect of the permanent magnet 403.

Furthermore, another coil (unillustrated) other than the above unillustrated coil is mounted on the electromagnet 402. The plunger 404 moves in a direction of going back to the frame 401 by charging this another coil with electricity (magnetizing the solenoid). Charging of another coil is stopped just after the plunger 404 moved. (The same is true to that the plunger moves in a direction of projecting out of the frame 401.) Energized force due to a compression spring 407 wound around a cover 406 which covers a side of another end of the plunger 404 (downward of FIGS. 7 to 9) maintains a pulled state in which the expanded diameter portion 405 of the plunger 404 is close to the frame 401.

A lever member 408 is fixed to the cover 406, and the lever member 408 moves integrally with the plunger 404. An end portion 409 of the lever member 408 has a function as a shield plate which shields a light path of a fixed, transmission typed, clamp lock detecting sensor 410 (a holding section lock sensor). Namely, as shown in FIG. 7, in a pulled state that the expanded diameter portion 405 of the plunger 404 is close to the frame 401, in which the pawl member 39 is allowed to release for opening from a locking state, since a light path is shielded by the end portion 409 of the lever member 408, the clamp lock detecting sensor 410 detects a state that clamp lock is canceled (a state that the pawl member 39 is releasable from a locking state due to the engagement roller 30). On the other hand, as shown in FIGS. 8 and 9, in a projecting state that the expanded diameter portion 405 of the plunger 404 projects out of the frame 401, in which the pawl member 39 is engaged in a locking state, since the end portion 409 of the lever member 408 does not shield a light path to allow a sensor light to transmit, the clamp lock detecting sensor 410 detects a locking state (a state that the pawl member 39 is locked by engaging with the engagement roller 30 to prohibit being released).

A clamp opening/closing detecting section 300, which detects an opened/closed state of the second clamp 7, namely, which detects whether the second clamp 7 is in a locking state or the second clamp 7 is in an opened state by canceling the locking state, is provided at an underside of the second lower jaw portion 80 and at a side of the clamp lock solenoid 400. Incidentally, when the second clamp 7 is in a locking state in which the pawl member 39 engages the engagement roller 30, the tip portion 39A of the pawl member 39 pushes one end side 302 of the lever member 301 in the clamp opening/closing detecting section 300 (a state shown in FIGS. 8 and 9).

A torsion coil spring 304 is provided at a pivot 303 of the lever member 301. The one end side 302 of the lever member 301 is energized by an effect of this spring 304 to move in a direction opposite to a pushing direction of the tip portion 39A of the pawl member 39. Another end side 305 of the lever member 301 has a function as a shield plate which shields a light path of a fixed, transmission typed, clamp opening/closing sensor 306. At a time of opening of the clamp as shown in FIG. 7, the another end side 305 of the lever member 301 shields a light path of the clamp opening/closing sensor 306, so that the clamp opening/closing sensor 306 detects that the clamp is in an opened state (a state that the pawl member 39 is released from a locking state with the engagement roller 30). On the other hand, at a time of closing of the clamp (a locking state) as shown in FIGS. 8 and 9, the another end side 305 of the lever member 301 does not shield a light path of the clamp opening/closing sensor 306 to allow a sensor light to transmit, so that the clamp opening/closing sensor 306 detects that the clamp is in a closed state (a locking state).

Figure 10:
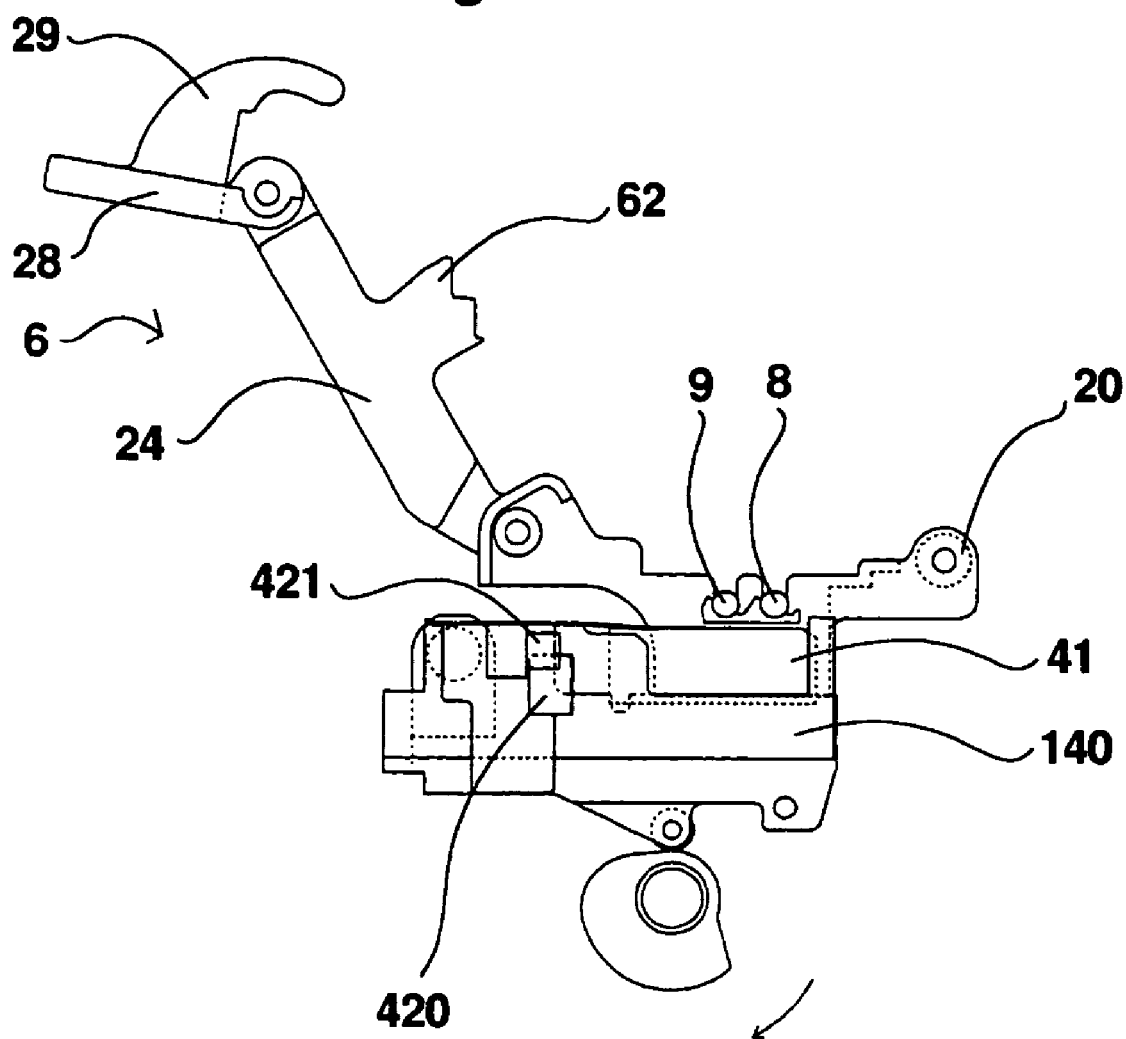
FIG. 10 is a left side view showing a state that a first clamp is opened.
Figure 11:
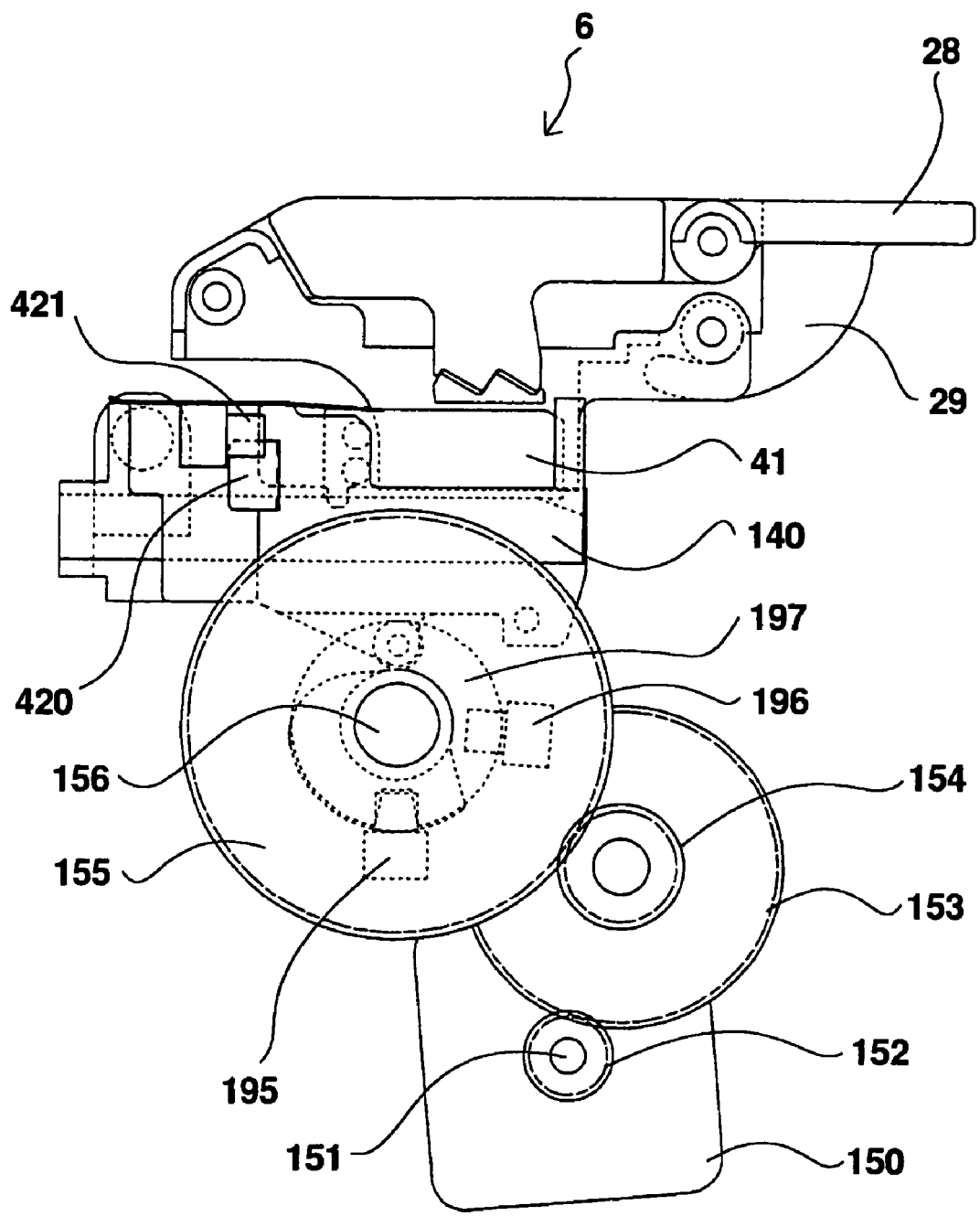
FIG. 11 is a left side view showing a state that the first clamp is closed and the wafer is located at the non-cutting position.
Figure 12:
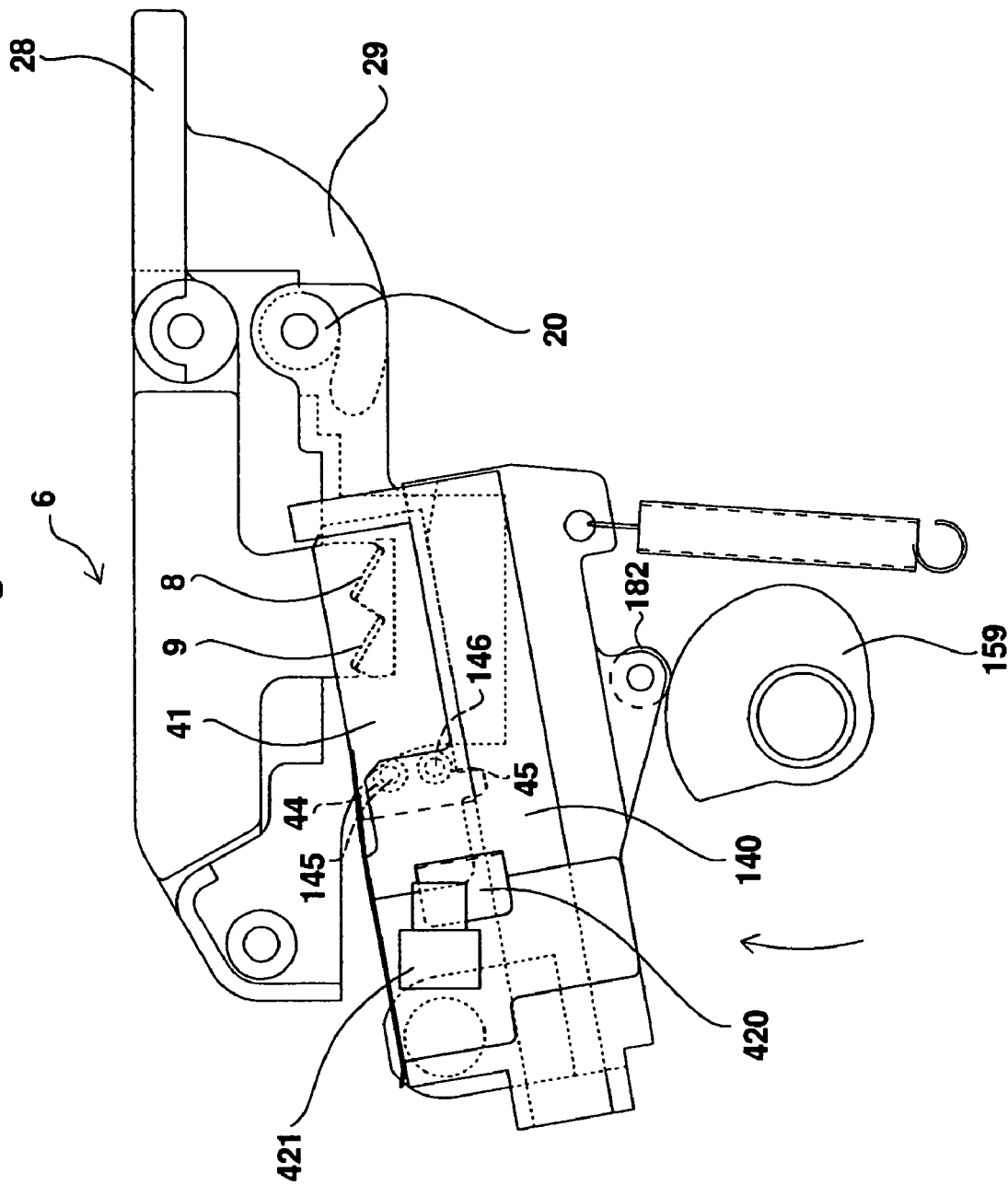
FIG. 12 is a left side view showing a state that the first clamp is closed and the wafer is located at the cutting position.

Further, as shown in FIGS. 10 to 12, a transmission type wafer position detecting sensor 421, which detects the wafer 41 and which serves as a cutting section detecting sensor, is disposed at a downward of the first clamp 6 located at a left side of the tube connecting apparatus 1, and a shield plate 420 provided integrally with the wafer holder 140 is disposed at a side of the wafer holder 140 facing the first clamp 6 (a downward of the first clamp 6). When the wafer holder 140 pivots (descends) due to the drive-conveying mechanism 200 to move the wafer 41 to a position (a cutting position) where the wafer 41 can cut the tubes 8, 9, the shield plate 420 shields a light path of the wafer position detecting sensor 421, so that the wafer position detecting sensor 421 detects that the wafer 41 (wafer holder 140) is in the cutting position (a state shown in FIG. 12).

On the other hand, as shown in FIGS. 10 and 11, when the wafer holder 140 is not driven so as to pivot (descend) by the drive-conveying mechanism 200, the wafer 41 is located at an initial position (a non-cutting position) where the wafer 41 can not cut the tubes 8, 9. In this state, the shield plate 420 does not shield a light path of the wafer position detecting sensor 421 to allow a sensor light to transmit, by a controlling unit 190 as stated later, the wafer 41 is judged to be located at the initial position where the wafer 41 can not cut the tubes 8, 9. In other words, the wafer position detecting sensor 421 detects that the wafer 41 (wafer holder 140) is in the downward initial position.

Furthermore, the tube connecting apparatus 1 is equipped with a controlling unit 190 for carrying out movement controlling of whole of the apparatus, a LCD display 192 for displaying a state of the apparatus to an operator and serving as a display section, a constant voltage power supply unit which converts commercial AC power source to DC power source which can drive/actuate actuators such as pulse motors and the like as well as the controlling unit 190.

Figure 13:
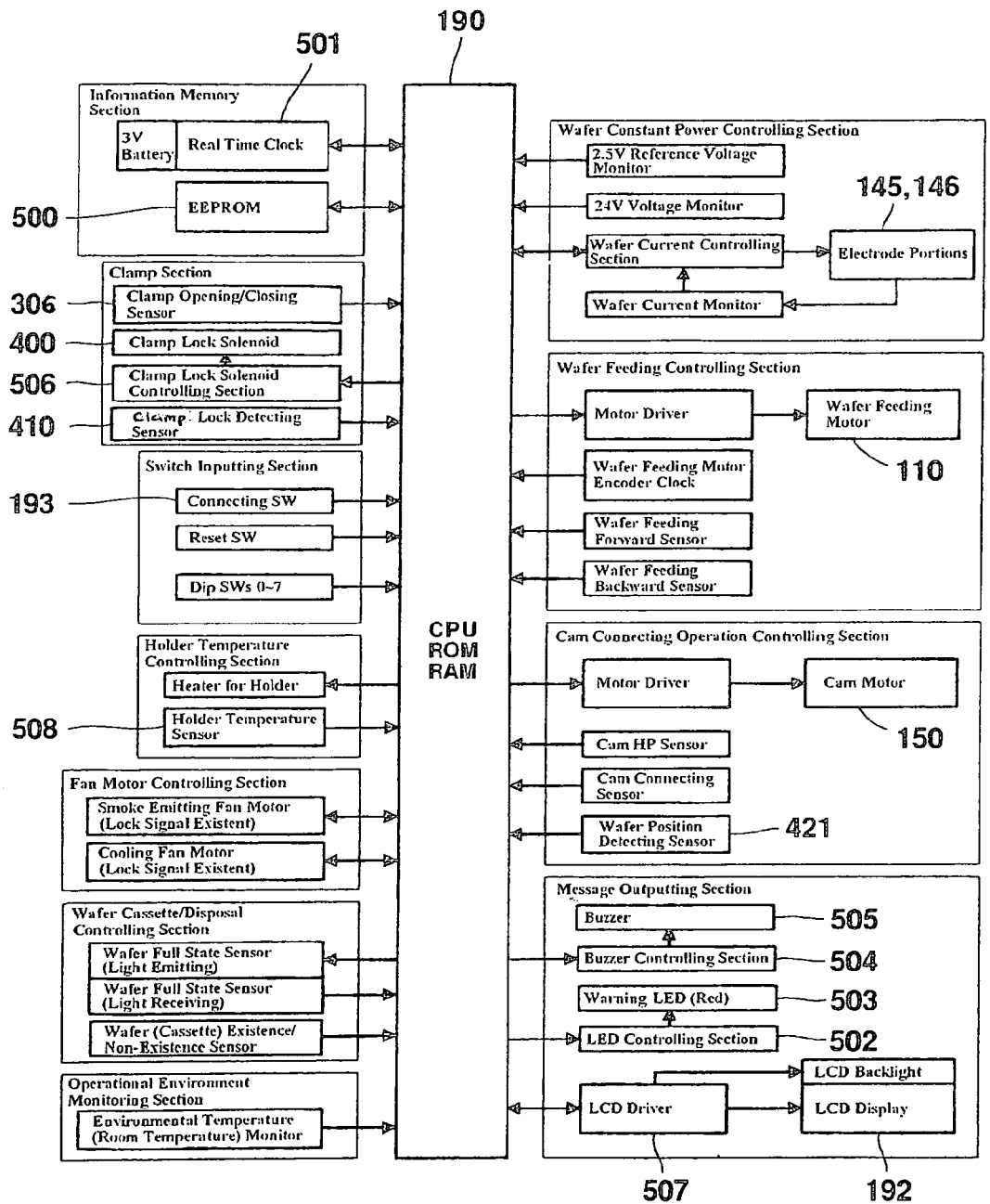
FIG. 13 is a schematic block diagram of a controlling section and each section of a control system.

As shown in FIG. 13, the controlling unit 190 is constituted with a CPU 191 which operates at a high clock speed as a central processing unit (See FIG. 3), a ROM in which controlling program and controlling data for the tube connecting apparatus 1 are memorized, a RAM which works as a work area for the CPU 191 and an internal bus which connects these.

An external bus is connected to the controlling unit 190. A information memory section for memorizing a connecting process state of the tubes, a clamp section which detects an opening/closing state or a locking state of the first clamp 6 and the second clamp 7 and which locks these clamps, a switch inputting section including a connecting switch 193 (See FIG. 3) that an operator instructs cutting and connecting operation to the tube connecting apparatus 1, a holder temperature controlling section for keeping the wafer holder 140 at a constant temperature, a fan motor controlling section which controls an unillustrated smoke emitting fan motor and an unillustrated cooling fan motor, a wafer cassette/disposal controlling section having sensors or the like for detecting existence or non-existence of the wafer 41 in the wafer cassette 120 or for detecting a full state of the used wafers 41 in the waste box 142, an operational environment monitoring section which monitors an environmental temperature (a room temperature) at which the tube connecting apparatus 1 is placed, a wafer constant power controlling section including a wafer current controlling section which controls current flowing between the electrode portions 145, 146, a wafer feeding controlling section which controls feeding operation of the wafers 41, a cam connecting operation controlling section having the wafer position detecting sensor 421 and a motor driver for driving a cam motor which rotates the driving shaft 156, and a message outputting section having a LCD driver 507 which controls operation or display of the LCD display 192 and the like are connected to the external bus. Incidentally, in FIG. 13, illustration for the external bus is omitted and a state that the controlling unit 190 and these sections are directly connected is shown.

The massage outputting section has the LCD display 192, the LCD driver 507 which controls a backlight of the LCD display 192 and an unillustrated inputting operation section, a LED controlling section 502 which turns on a red colored caution LED 503 for noticing maintenance timing of the tube connecting apparatus 1, and a buzzer controlling section 504 which actuates a buzzer 505 to give a warning sound when a maintenance day lapsed.

The information memory section has an EEPROM 500 serving as a non-volatile memory and a real time clock 501 which actuates under a 3V power source. In the EEPROM 500, information with respect to a connecting process state of the tubes 8, 9 (information expressing being in a state of connecting operation or information expressing being in a state of non-connecting operation), exchange information of the wafer 41 (information expressing being exchanged or information expressing being unexchanged), a date, which is arbitrarily set via an unillustrated inputting operation section connected to the LCD driver 507, for a periodic check or maintenance such as part replacement or the like of the tube connecting apparatus 1, a predetermined number of accumulated connecting operations of the tubes 8, 9 (an accumulated number that the tube connecting apparatus 1 carried out connecting operation) and the like are memorized.

The clamp section is constituted by equipping the above stated clamp opening/closing sensor 306, the clamp lock detecting sensor 410 and a clamp lock solenoid controlling section 506 which controls actuation of the clamp lock solenoid 400. Further, the switch inputting section has, other than the above stated connecting switch 193, a reset switch 194 for reset operation of the tube connecting apparatus 1 when power source is supplied to the tube connecting apparatus 1 again after power supply is shut off during connecting operation of the tubes 8, 9, and dip switches 0 to 7 for switching to test modes and the like in which adjustment in assembling of the tube connecting apparatus 1 is carried out.

(Operation)

Figure 14:
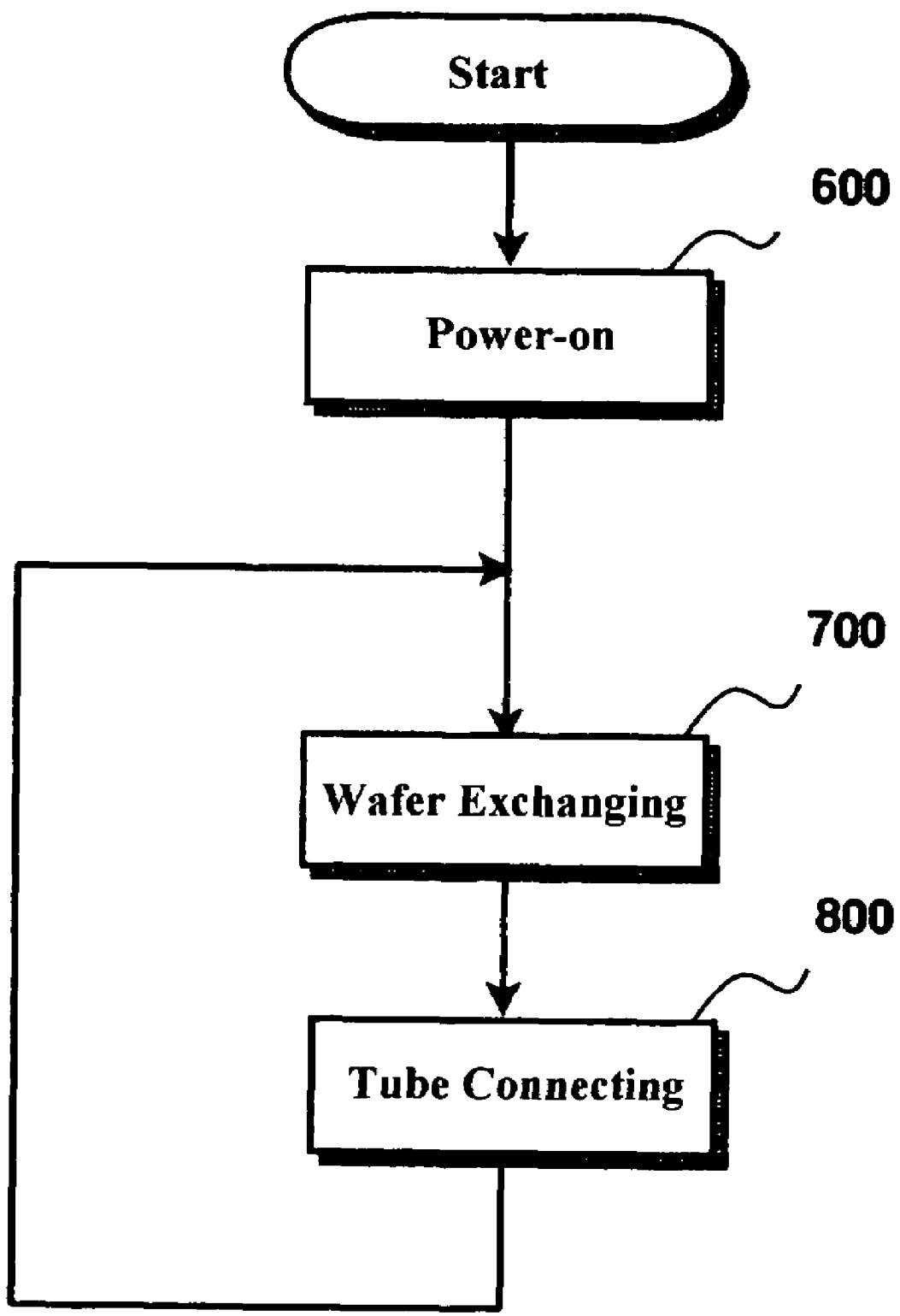
FIG. 14 is a flowchart of a tube connecting routine executed by a CPU of the controlling section.

Next, with respect to operation of the tube connecting apparatus 1 in this embodiment, operation carried out by the CPU 191 in the controlling unit 190 will be explained. Incidentally, when electric power is inputted to the controlling unit 190 via an unillustrated switch, the CPU 191 reads out the controlling program and the controlling data from the ROM and develops them at the RAM, and then executes a tube connecting routine for cutting and connecting the tubes 8, 9 as shown in FIG. 14.

Figure 15:
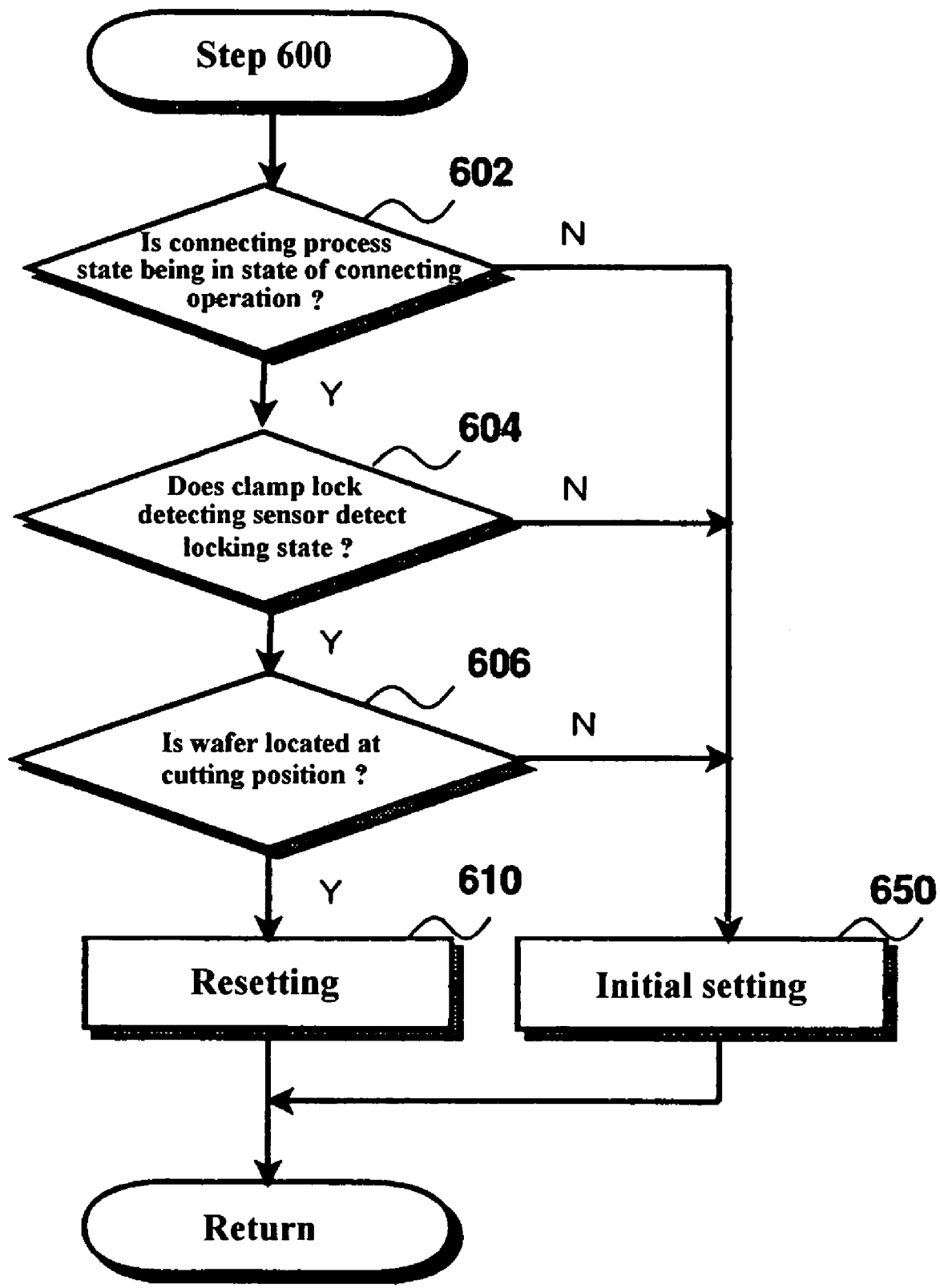
FIG. 15 is a flowchart of a power-on subroutine showing details of step 600 in the tube connecting routine.

In this tube connecting routine, first, in step 600, the CPU 191 carries out a power-on subroutine. As shown in FIG. 15, in the power-on subroutine, in step 602, the CPU 191 reads out the information with respect to a connecting process state (information expressing being in a state of connecting operation or non-connecting operation) memorized in the EEPROM 500, then judges as to whether or not the information with respect to a connecting process state is information expressing being in a state of connecting operation. When an affirmative judgment is made, the CPU 191 judges as to whether or not the clamp lock detecting sensor 410 detects the locking state in the next step 604. When the judgment in step 604 is affirmative, the CPU 191 judges as to whether or not the wafer position detecting sensor 421 detects the wafer 41 located at the cutting position.

The CPU 191, when electric power is inputted, in accordance with the judgment results in steps 602 to 606, judges correctly whether or not power supply to the tube connecting apparatus 1 was shut (cut) off during last connecting operation of the tubes 8, 9 (before electric power is inputted). The CPU 191, as stated later, drives the EEPROM 500 to memorize the latest process state of the tube connecting operation. (See steps 814 and 826 in FIG. 19.) In step 602, if information with respect to the latest connecting process state read out from the EEPROM 500 is being in a state of connecting operation, it is likely that connecting process was not finished because power supply was shut off during last connecting operation. (If the connecting process was finished, the information with respect to the connecting process state read out from the EEPROM 500 must be information expressing being in a state of non-connecting operation.) Further, in step 604, when the clamp lock detecting sensor 410 detects the locking state, since the expanded diameter portion 405 of the clamp lock solenoid 400 which is the self-holding type solenoid is in the state of prohibiting the pawl member 39 from opening movement as stated above, it is likely that power supply was shut off during last tube connecting operation. (If the connecting process was finished, the clamp lock detecting sensor 410 does not detect the locking state.) Furthermore, in step 606, when the wafer position detecting sensor 421 detects the wafer 41 located at the cutting position, since the wafer 41 was moved to the position that the wafer 41 can cut the tubes 8, 9 as stated above, it is likely that power supply was shut off during last tube connecting operation. (If the cutting operation was finished, since the wafer 41 was located at the non-cutting position, the wafer position detecting sensor 421 must not detect the wafer 41.) Accordingly, in steps 602 to 606, the CPU 191 judges correctly whether or not power supply to the tube connecting apparatus 1 was shut off during last connecting operation based upon a plurality of judgments.

An affirmative judgment is made in step 606, since the tube connecting apparatus 1 was in a state that power supply was shut off during last tube connecting operation, in step 610, the CPU 191 executes a resetting subroutine for resetting the tube connecting apparatus 1 to a normal state such that the tube connecting apparatus 1 can carry out the tube connecting operation.

Figure 16:
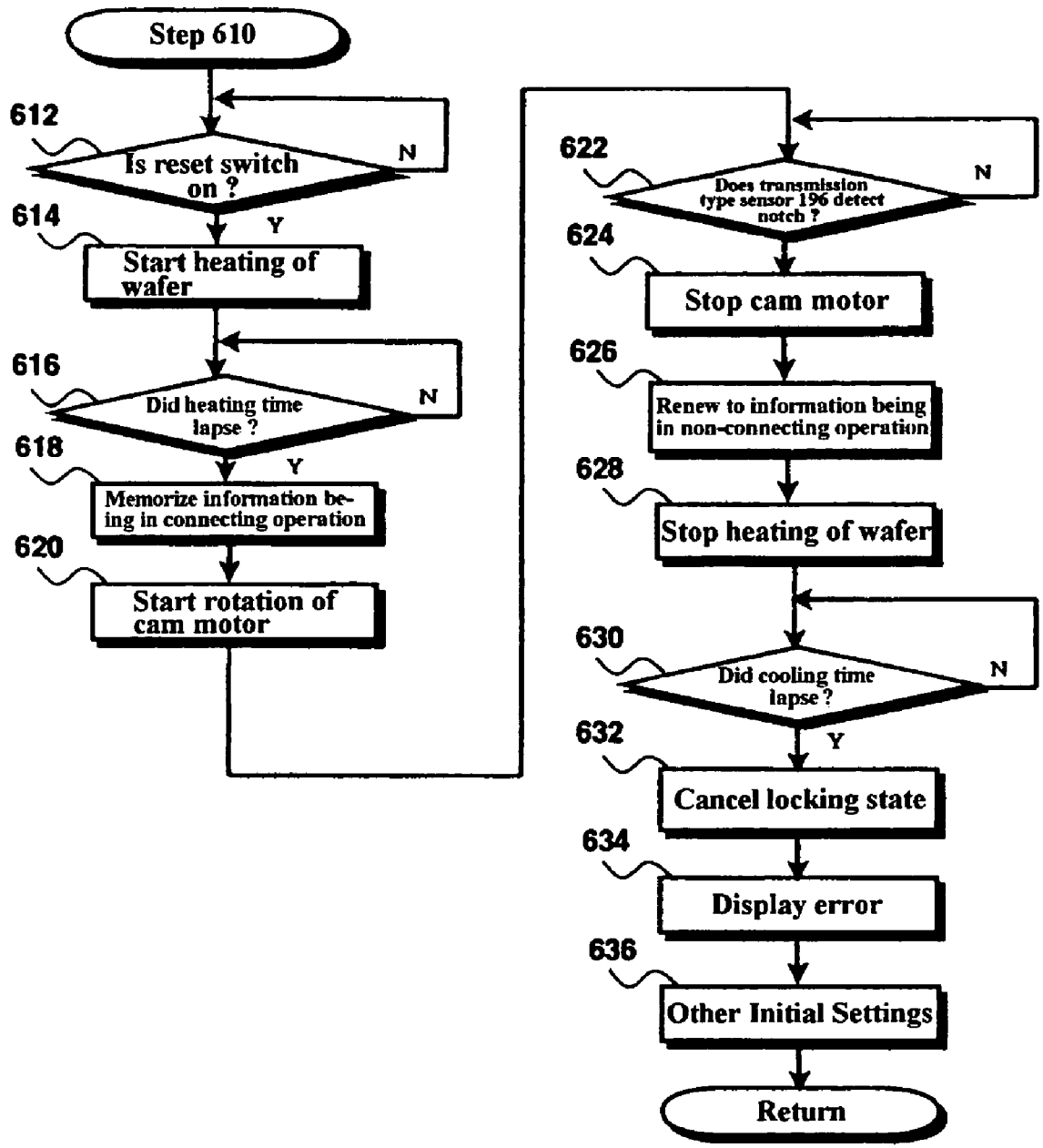
FIG. 16 is a flowchart of a resetting subroutine showing details of step 610 in the power-on subroutine.

As shown in FIG. 16, in the resetting subroutine, first in step 612, the CPU 191 waits until the reset switch 194 is pushed (tuned on) by an operator. When the reset switch 194 is pushed, the CPU 191 drives the wafer current controlling section to supply electricity to the wafer 41 via the electrode portions 145, 146 in order to start heating of the wafer 41 in the next step 614, then in step 616, waits until predetermined heating time lapses. When the predetermined time lapses, in step 618, the CPU 191 drives the EEPROM 500 to memorize information expressing being in a state of tube connecting operation (e.g., "1") as the information with respect to a connecting process state.

Next in step 620, the CPU 191 drives the cam motor 150, then in step 622, judges as to whether or not the transmission type sensor 196 detects the notch 198. When a negative judgment is made, the CPU 191 continues to drive the cam motor 150, while when an affirmative judgment is made, the CPU 191 stops driving of the cam motor 150 in step 624. Then in step 626, the CPU 191 makes the EEPROM 500 to renew the information with respect to a connecting process state from the information expressing being in a state of tube connecting operation to information expressing being in a state of tube non-connecting operation (e.g., "0")), subsequently in step 628, makes the wafer current controlling section to stop electricity supply to the wafer 41 in order to stop heating of the wafer 41.

In the next step 630, the CPU 191 waits until predetermined time (cooling time) that the wafer 41 is cooled down lapses. When the cooling time lapses, the CPU 191 drives the clamp lock solenoid 400 to cancel the locking state (makes the plunger 404 in the pulled state). As stated above, in steps 614 to 612, the CPU 191 heats the wafer 41 again and fuses the tubes 8, 9 adhered to the wafer 41 in order to finish connecting of the tubes 8, 9. However, because connecting strength and sterilized connecting of the tubes 8, 9 are not secured, in the next 634, the CPU 191 makes the LCD display 192 to display error indication via the LCD driver 507 and drives the buzzer controlling section 504 to make the buzzer 505 to give a sound in order to draw operator's attention. Next in step 636, the CPU 191 carries out various other initial settings, then the resetting subroutine and the power-on subroutine are finished to proceed to step 700 in FIG. 14.

Figure 17:
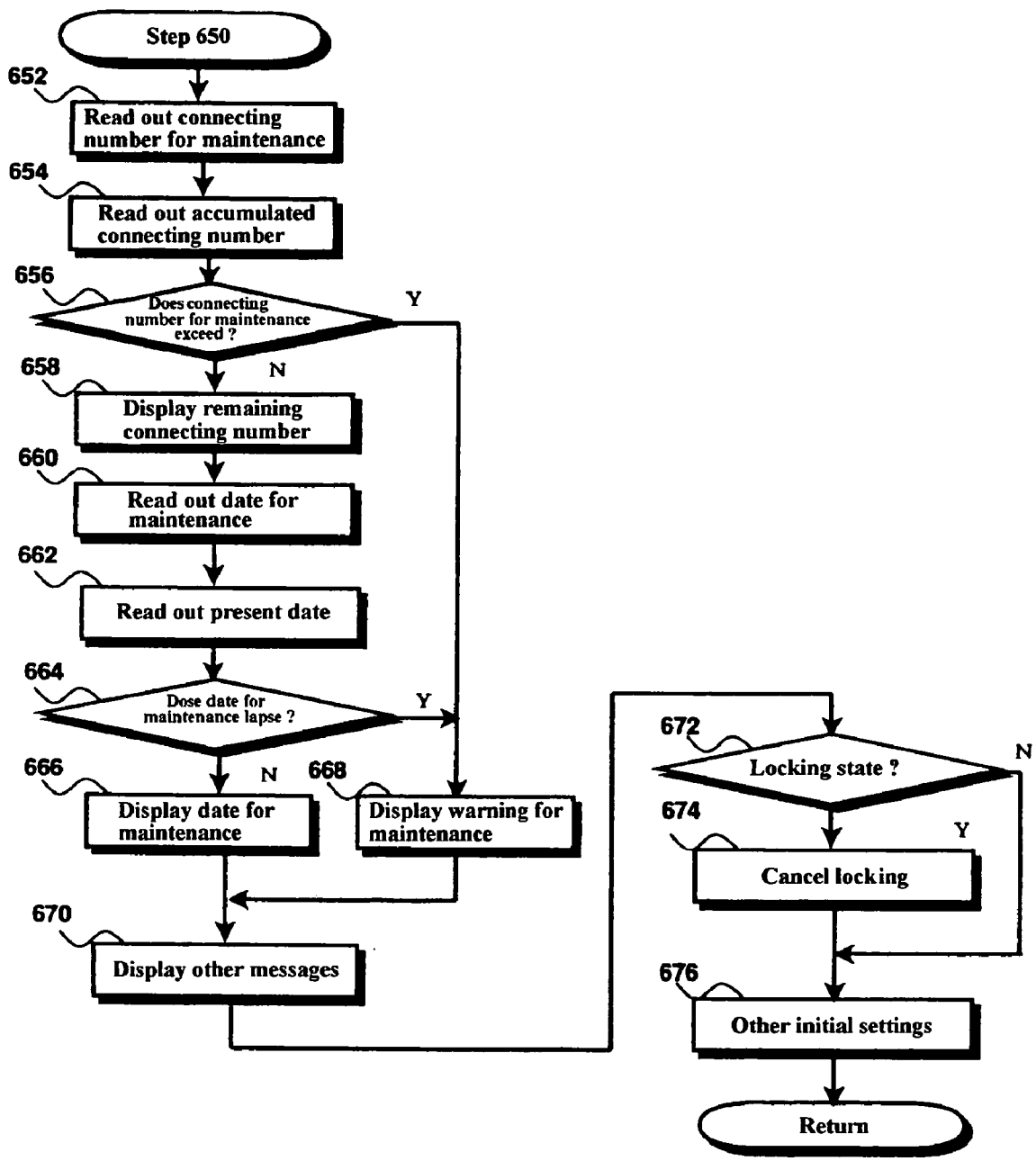
FIG. 17 is a flowchart of an initial setting subroutine showing details of step 650 in the power-on subroutine.

On the other hand, a negative judgment is made in step 602, 604 or 606 in FIG. 15, then in step 650, the CPU 191 executes an initial setting subroutine for executing initial setting in a normal state. As shown in FIG. 17, in the initial setting subroutine, the CPU 191 reads out the predetermined connecting number that maintenance becomes necessary from the EEPROM 500 in step 652, and reads out the accumulated connecting number memorized in the EEPROM 500 last time (See step 834.) in step 654. Then in step 656, the CPU 191 compares the connecting number for maintenance with the accumulated connecting number to make a determination as to whether or not the accumulated connecting number exceeds the connecting number for maintenance. When a negative determination is made, the subroutine proceeds to step 668, while when an affirmative determination is made, the CPU 191 makes the LCD display 192 to display a remaining connecting number that maintenance becomes necessary in the next step 658.

Next, in step 660, the CPU 191 reads out the date for maintenance memorized in the EEPROM 500 in advance, then in step 662, reads out the present date from the real time clock 501 to make a determination in step 664 as to whether or not the present date lapsed the date for maintenance. When an affirmative determination is made, the subroutine proceeds to step 668, while when a negative determination is made, the CPU 191 makes the LCD display 192 to display the date for maintenance in the next step 666 to proceed to step 670.

In step 668, because the accumulated connecting number exceeds the connecting number for maintenance or the date for maintenance lapsed, the CPU 191 makes the LCD display 192 to display a warning that maintenance is necessary and controls the LCD controlling section 502 to light on or light on and off the red colored warning LED 503.

In step 670, the CPU 191 makes the LCD display 192 to display other messages such as a reference time that the tube connecting apparatus 1 can start operation and the like, then in the next step 672, judges as to whether or not the clamp lock detecting sensor 410 detects the locking state of the clamp lock solenoid 400. When a negative judgment is made, the subroutine advances to step 676. When an affirmative judgment is made, the CPU 191 cancels the locking state of the clamp lock solenoid 400 in step 674. In step 676, the CPU 191 carries out various other initial settings, then the initial setting subroutine and the power-on subroutine are finished to proceed to step 700 in FIG. 14.

Figure 18:
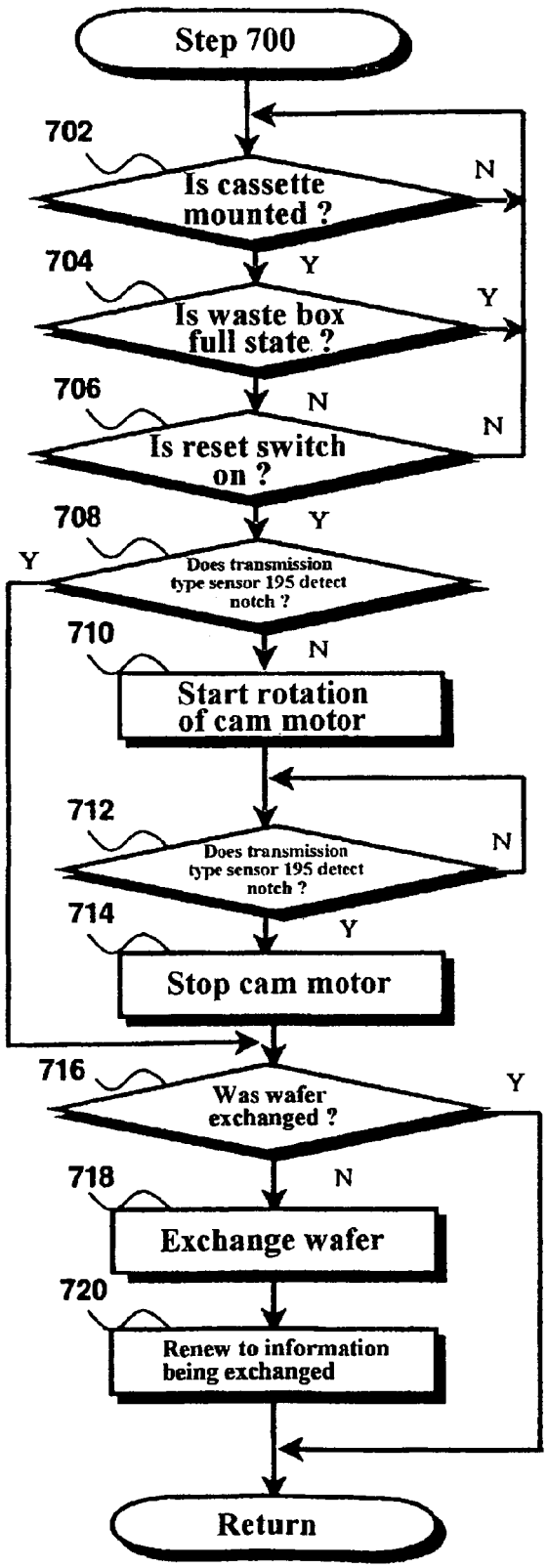
FIG. 18 is a flowchart of a wafer exchanging subroutine showing details of step 700 in the tube connecting routine.

In step 700, a wafer exchanging subroutine for exchanging the wafers 41 is carried out. As shown in FIG. 18, in the wafer exchanging subroutine, the CPU 191 judges as to whether or not the wafer cassette detecting sensor 121 detects the wafer cassette 120. When a negative judgment is made, the CPU 191 waits until the wafer cassette 120 is mounted, while when an affirmative judgment is made, the CPU 191 judges in the next step 704 as to whether or not the wafer full state sensor 143 of a light receiving side detects a state in which transmission is shut off (a state that the wafers 41 disposed of (accommodated) to the waste box 142 are full). When an affirmative judgment is made, the subroutine returns to step 702, while when a negative judgment is made, the CPU 191 waits until the reset switch 194 is pushed in the next 706. Incidentally, in this embodiment, before waiting in steps 702 to 706, the CPU 191 makes the LCD display 192 to display that the wafer cassette 120 is not mounted, that the waste box 142 is full, and that the reset switch 194 be pushed, respectively, which is not shown in FIG. 18.

When a judgment that the reset switch 194 is pushed is made in step 706, the CPU 191 judges in the next step 708 as to whether or not the transmission type sensor 195 detects the notch 198, namely, whether or not the cam 157 or the like is in the initial position. When an affirmative judgment is made, the subroutine proceeds to step 716, while when a negative judgment is made, the CPU 191 makes the cam motor 150 to start to rotate in step 710. The CPU 191 continues to make the cam motor 150 to rotate until the transmission type sensor 195 detects the notch 198 in step 712, and when the transmission type sensor 195 detects the notch 198, the CPU 191 stops rotation of the cam motor 150 in step 714.

Next, in step 716, the CPU 191 reads out the exchange information of the wafer 41 from the EEPROM 500 and judges as to whether or not the exchange information of the wafer 41 is the information expressing being exchanged (e.g., "1"). When an affirmative judgment is made, the wafer exchanging subroutine is finished to proceed to step 800 in FIG. 14. When a negative judgment is made, the CPU 191 drives the wafer feeding motor 110 to carry out exchange of the wafers 41 in step 718.

The exchange of the wafers 41 carried out in step 718 will be explained in detail. As stated above, the wafer feeding member 115 which is moved by rotation driving of the wafer feeding motor 110 moves reciprocally between the wafer feeding start position and the wafer feeding end position according to normal and reverse rotation of the wafer feeding motor 110. At this time, the CPU 191 detects a position of the wafer feeding member 115 located between the wafer feeding start position and the wafer feeding end position at a time of normal rotation of the wafer feeding motor 110 with the transmission type sensor 131 one pulse by one pulse in accordance with the revolving amount of the revolving plate 130 which is linked directly with the rotation of the wafer feeding motor 110. Namely, by detecting the piece to be detected 119 of the wafer feeding member 115 which is located at the wafer feeding start position with the transmission type sensor 132, and based on the wafer feeding start position, by detecting the moving amount of the wafer feeding member 115 through the revolving amount of the revolving plate 130 with the transmission type sensor 131, the CPU 191 grasps as to where the wafer feeding member 115 is located.

The CPU 191 judges as to whether or not the wafer feeding member 115 moves more than a predetermined amount (30mm in this embodiment, See the wafer feeding member 115 shown by a two dotted line in FIG. 25.) from the wafer feeding start position to a direction of the wafer feeding end position. When a negative judgment is made, the CPU 191 continues to grasp the position of the wafer feeding member 115. Incidentally, in this embodiment, the moving amount of the wafer feeding member 115 for feeding the wafer 41 is set to approximately 55 mm.

When an affirmative judgment is made, the CPU 191 judges as to whether or not a difference between a predetermined number of pulses and an actually detected number of pulses, which is not less than predetermined pulses (ex. 20 pulses), occurred, namely, the CPU 191 judges as to whether or not the actually detected number of pulses was less than 20 pulses to the predetermined number of pulses. When an affirmative judgment is made, the CPU 191 determines that feeding malfunction of the wafer 41 occurred and waits until the reset switch 194 is pushed. When a negative judgment is made, the CPU 191 determines that normal feeding was made.

When feeding malfunction of the wafer 41 is determined, the CPU 191 stops driving of the wafer feeding motor 110 and makes the LCD display 192 to display feeding malfunction of wafer and indication that the wafer is to be removed, and drives the cam motor 150 by a predetermined amount reversely opposing to the normal driving carried out at the time of a series of tube connecting operation to locate the cam 158 at a predetermined position so that the notched portion 178 formed at the cam 158 faces the bearing 172. (See FIG. 25(C).) Thus, the bearing 172 is ready to advance into the notched portion 178. In other words, the second clamp 7 is allowed to move to an evacuating position in a right direction of an arrow B in FIG. 3 (a direction that allows the second clamp 7 to move in a direction opposite to a direction of the second clamp 7 at the time of connecting the tubes). (In this embodiment, the second clamp 7 is allowed to move by approximately 4 mm.) At this moment, both of the transmission type sensors 195, 196 are in a state that they are shielded by the revolving plate 197. (See FIG. 6(C).)

An operator can move the second clamp 7 to the evacuating position and remove the wafer which caused feeding malfunction such as double feeding of the wafers 41 by accessing a space defined between the first clamp 6 and the second clamp 7. (See FIG. 25(D).) Incidentally, when the operator pushes the reset switch 194 after finishing the error cancellation operation, the CPU 191 fetches a signal thereof, then drives the motors 110, 150 to reset various mechanisms to an initial state.

In the next step 720, the CPU 191 makes the EEPROM 500 to renew the exchange information of the wafer 41 from the information expressing being unexchanged (e.g., "0") to the information expressing being exchanged, then the wafer exchanging subroutine is finished to proceed to step 800 in FIG. 14.

Figure 19:
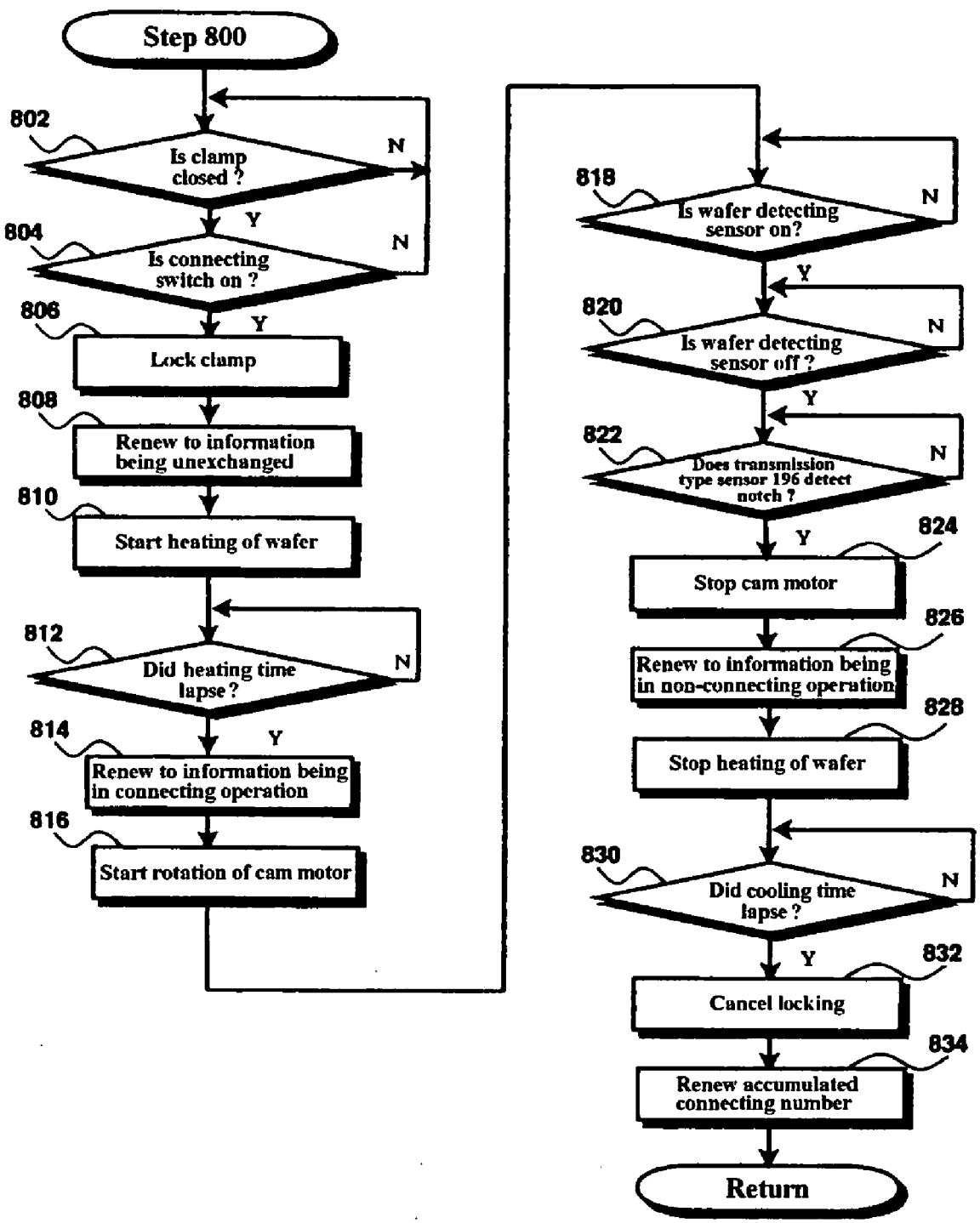
FIG. 19 is a flowchart of a tube connecting subroutine showing details of step 800 in the tube connecting routine.

In step 800, the CPU 191 executes a tube connecting subroutine for cutting and connecting the tubes 8, 9. As shown in FIG. 19, in this tube connecting subroutine, first, in step 802, the CPU 191 judges as to whether or not the clamp opening/closing sensor 306 detects that the second clamp 7 (and the first clamp 6 linked by the long hole 40 and the shaft 19) is in a closed state, namely, whether or not the pawl member 39 engages the engagement roller 30. When a negative judgment is made, the CPU 191 makes the LCD display 192 to display indication for urging an operator that tubes 8, 9 are to be put into the grooves 22, 23 and then the first clamp 6 and the second clamp 7 are to be closed (unillustrated in FIG. 19), then keeps a waiting state.

Figure 20:
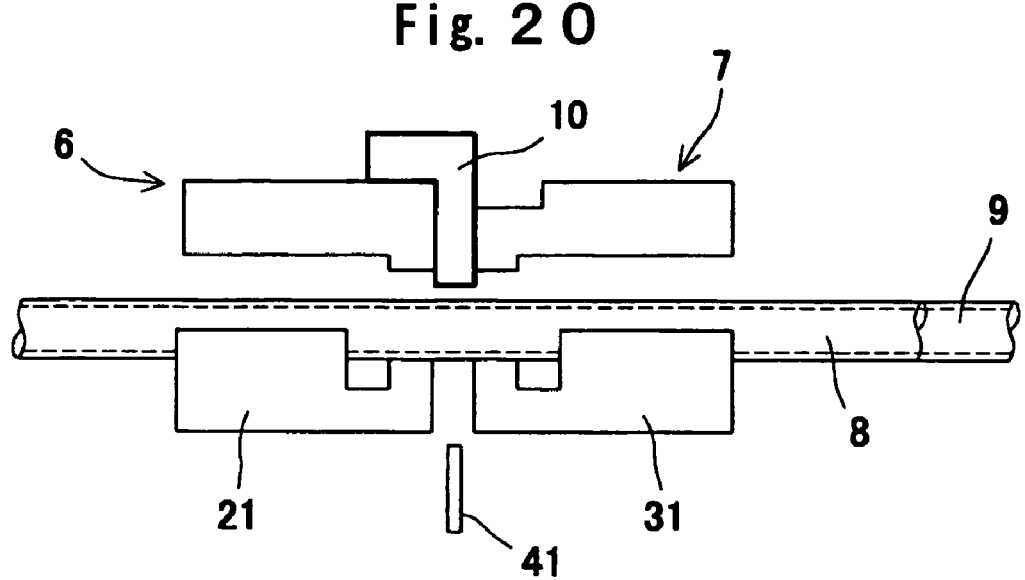
FIG. 20 is an explanatory drawing showing operation 1 of main sections of the tube connecting apparatus and a front view illustratively showing a state that covering bodies of the first clamp and the second clamp begin to be closed.
Figure 21:
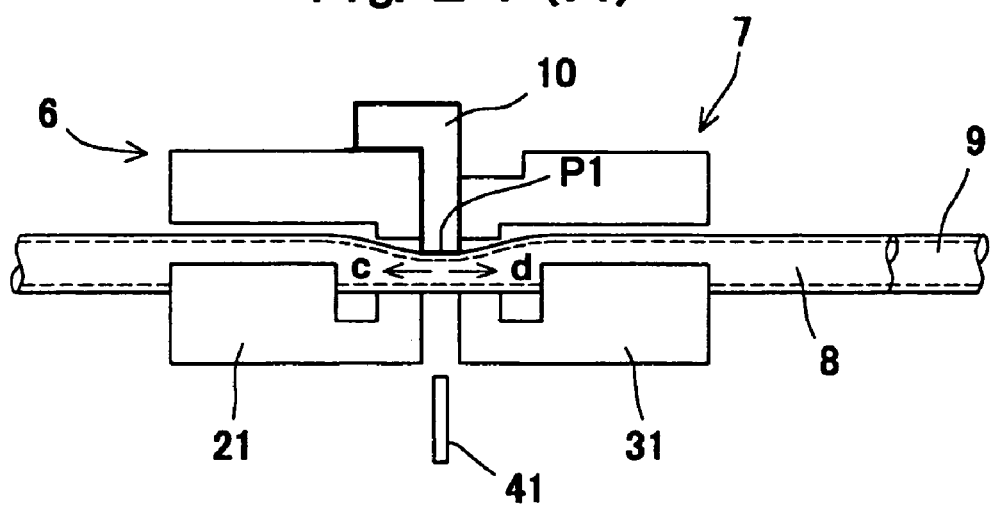
FIG. 21 is a front view illustratively showing operations for the main sections of the tube connecting apparatus, FIG. 21(A) showing operation 2 thereof and FIG. 21(B) showing operation 3 thereof.
Figure 21:
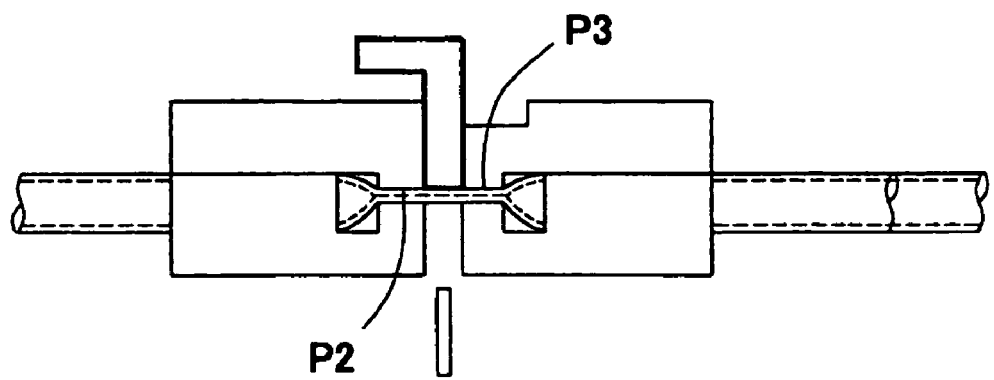

An operator puts the tubes 8, 9 into the grooves 22, 23, then carries out operation for closing the covering body 24 of the first clamp 6 and the covering body 34 of the second clamp 7 (See FIG. 20.) When the operator closes either one of the covering body 24 of the first clamp 6 or the covering body 34 of the second clamp 7, because the shaft 19 is inserted into the long hole 40, another of the covering body 24 of the first clamp 6 or the covering body 34 of the second clamp 7 is linked to close approximately at the same time. When the operator further continues to carry out the operation for closing the covering body 24 and the covering body 34, the tip portion 12 of the tube-pushing member 10 firstly abuts and then deforms the tubes 8, 9, which are put in a parallel state at a first position P1 that is an abutting position, to a flat state. (See FIG. 21(A).) At this moment, blood inside the tubes 8, 9 at a portion which was pressed by the tube-pushing member 10 is pushed out such that it is excluded in directions of an arrow c and an arrow d in FIG. 21(A).

Subsequently, when the operation for closing the covering body 24 and the covering body 34 is carried out further to engage a tip portion 29A of the pawl member 29 of the engagement mechanism 26 in the first clamp 6 with the engagement roller 20, the first clamp 6 presses and holds the tubes 8, 9 to a flat state with predetermined pressing force at a second position P2 which is adjacent to the first position P1. At this time, the tube-pushing member 10 disposed so as to contact the first clamp 6 also presses the tubes 8, 9 to an almost squashed state (a state that blood inside the tubes hardly exits) in the same manner as the first clamp 6. (See FIG. 21(B).)

FIG. 23(A) shows a state that the covering body 24 of the first clamp 6 is closed to the tubes 8, 9 put in the grooves 22, 23 and a state just before the tip portion 12 of the tube-pushing member 10 presses tubes 8, 9 to a flat state. As shown in FIG. 23(B), when the operator continues the operation for closing the covering body 24, the tip portion 12 of the tube-pushing member 10 presses the tubes 8, 9 to a flat state. At this time, pressing operation by the first clamp 6 and the second clamp 7 to the tubes 8, 9 is carried out continuously in a linked manner.

Further, because movement of the second clamp 7 is linked with movement of the first clamp 6, operation for closing the covering body 34 of the second clamp 7 is carried out approximately at the same time of the operation for closing the covering body 24 of the first clamp 6. When the tip portion 39A of the pawl member 39 engages the engagement roller 30 according to the engagement mechanism 36 in the second clamp 7, the second clamp 7 which is located so as to contact the tube-pushing member 10, in the same manner as the first clamp 6, presses and holds the tubes 8, 9 to a flat state in an almost squashed state (a state that blood inside the tubes hardly exits) with predetermined pressing force at a third position P3 which is adjacent to the first position P1 and which is a position opposing to the second position P2 via the first position P1. Thus, blood inside the tubes 8, 9 from the second position P2 to the third position P3 via the first position P1, namely, blood inside the tubes 8, 9 at portions being equivalent from a portion pressed by the first clamp 6 to a portion pressed by the second clamp 7 via the tube-pushing member 10 is almost excluded. (See FIG. 21(B).)

Figure 25A:
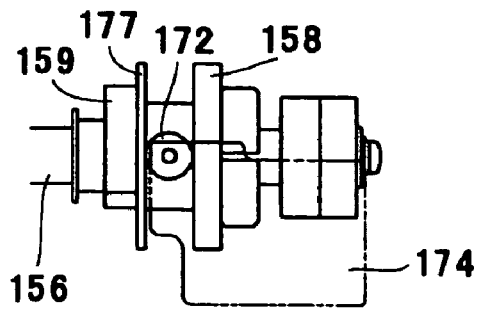
FIG. 25 is an enlarged plan view showing around a cum which regulates movement of the second clamp, FIG. 25(A) showing an initial state, FIG. 25(B) showing a finished state of connecting operation, FIG. 25(C) showing a state that a notched portion faces the bearing and FIG. 25(D) showing a state that the second clamp is moved to an evacuated position.
Figure 25B:
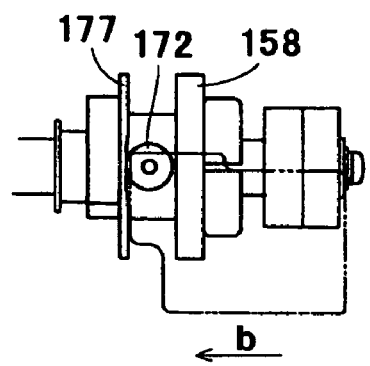
Figure 25C:
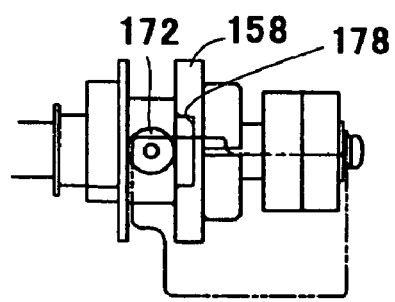
Figure 25D:
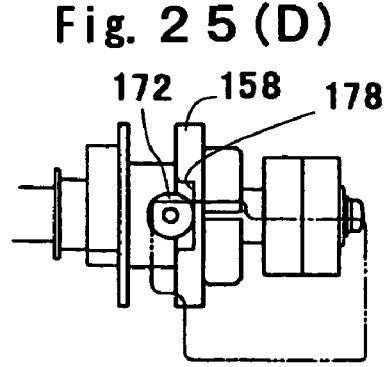
Figure 26:
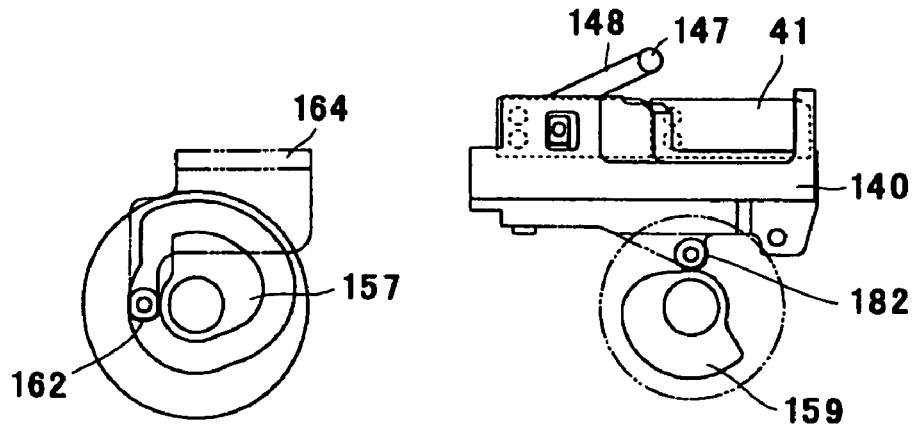
FIG. 26 is a side view of a cam which regulates movement of the first clamp and a cam which regulates movement of the wafer holder, FIG. 26(A) showing an initial state, FIG. 26(B) showing a cutting state, and FIG. 26(C) showing a state that cutting is finished or connecting is started.
Figure 26:
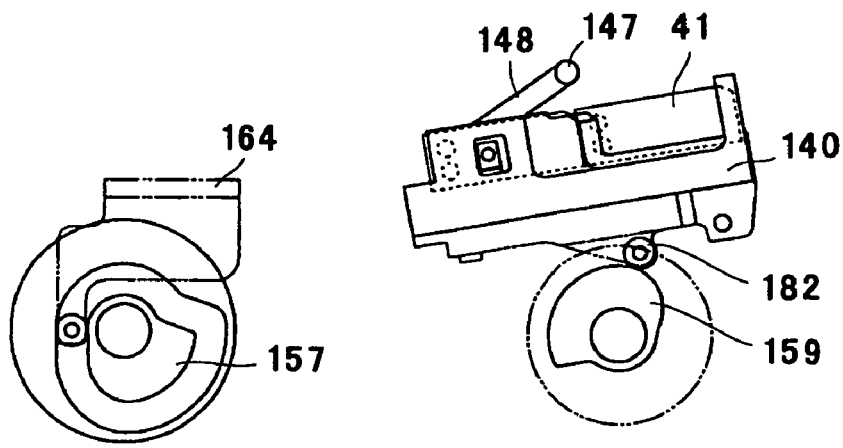
Figure 26:
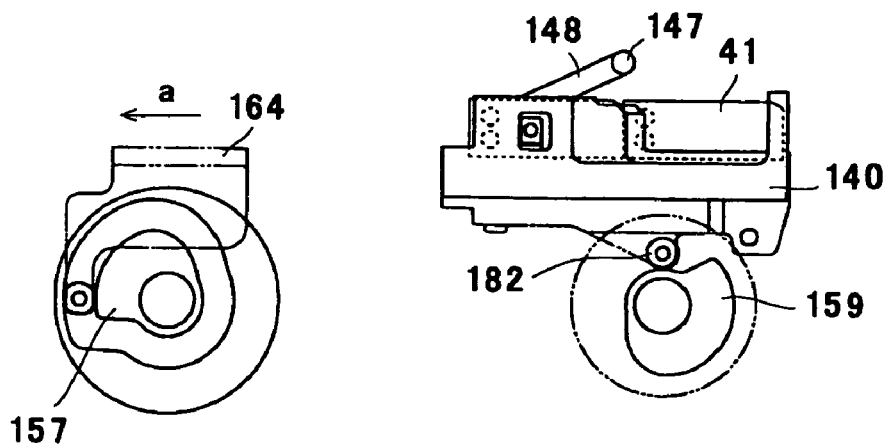

When an affirmative judgment is made in step 802, the CPU 191 judges as to whether or not the connecting switch 193 is turned on in the next step 804. When a negative judgment is made, the CPU 191 makes the LCD display 192 to display indication for urging operator to push the connecting switch 193 (unillustrated in FIG. 19) and keeps a waiting state. When an affirmative judgment is made in step 804, the CPU 191 makes the clamp lock solenoid controlling section 506 to magnetize the clamp lock solenoid 400. This brings the plunger 404 to project upward to engage the expanded diameter portion 405 with the pawl member 39 so as to prohibit opening movement of the pawl member 39, thereby the second clamp 7 comes to the locking state in which opening movement is prohibited. Incidentally, because the first clamp 6 is linked with the second clamp 7 as stated above, the first clamp also comes to the locking state in which opening movement is prohibited. In this state, FIGS. 8 and 11 respectively show a state of the second clamp 7 and the first clamp 6, and the FIGS. 25(A) and 26(A) show a state of the cam 158 and the cams 157, 159.

Next, in step 808, the CPU 191 makes the EEPROM 500 to renew information with respect to the exchange information of the wafer 41 from the information expressing being exchanged to the information expressing being unexchanged. In the next step 810, the CPU 191 supplies electricity to the wafer 41 via the electrode portions 145, 146 to start heating of the wafer 41, and waits until predetermined heating time lapses in step 812. When the predetermined time lapses, the CPU 191 renews the information with respect to the connecting process state in the EEPROM 500 from the information expressing being in a state of non-connecting operation to the information expressing being in a state of connecting operation.

Subsequently, the CPU 191 drives the cam motor 150 in step 816 and waits until the wafer detecting sensor 421 detects the wafer 41 (wafer holder 140) in step 818. When the wafer detecting sensor 421 detects the wafer 41, the CPU 191 waits until the wafer detecting sensor 421 does not detect the wafer 41 in step 820 due to descending of the wafer 41, then judges in step 822 as to whether or not the transmission type sensor 196 detects the notch 198. When a negative judgment is made, the CPU 191 keeps driving of the cam motor 150, while when an affirmative judgment is made, the CPU 191 stops driving of the cam motor 150 in step 824.

In these steps 816 to 826, cutting and connecting of the tubes 8, 9 are carried out by the tube connecting apparatus 1, and details thereof are as follows: The CPU 191 drives the cam motor 150, which makes the cam 158 and the cams 157, 159 to start rotating in a predetermined direction, yet the cam 158 retains a state shown in FIG. 25(A) for a predetermined period of time. During this period, the wafer holder 140 swings according to rotation of the cam 159 to ascend a predetermined distance between the first clamp 6 and the second clamp 7. (See FIG. 26(B).) Accompanied by this ascending movement, the roller 147 ascends and the supporting member projection portion 14 which abuts the roller 147 also ascends.

Figure 22A:
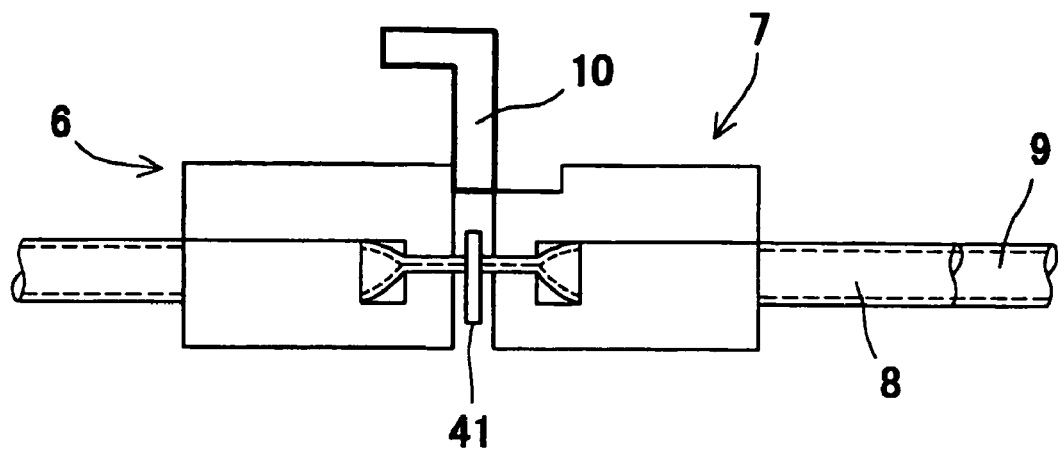
FIG. 22 is a front view illustratively showing operations for the main sections of the tube connecting apparatus, FIG. 22(A) showing operation 4 thereof, FIG. 22(B) showing operation 5 thereof and FIG. 22(C) showing operation 6 thereof.
Figure 22B:
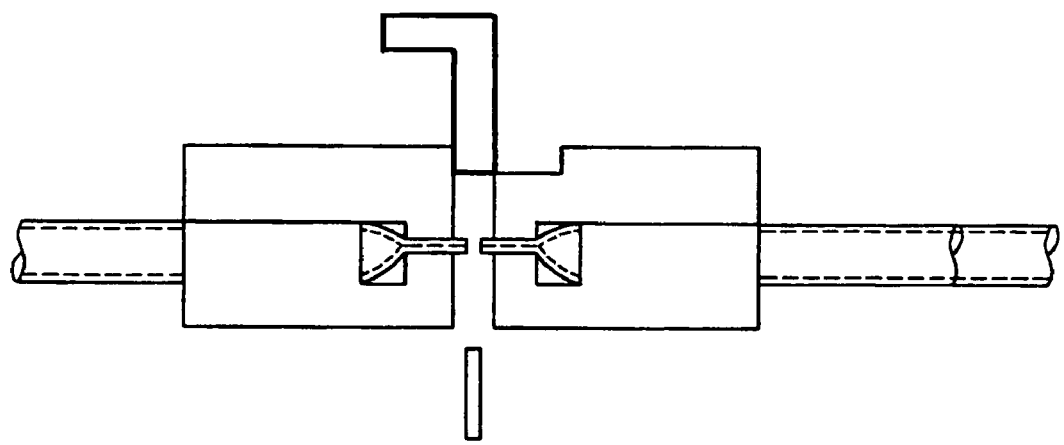

As shown in FIG. 22(A), the projection portion 148 which has the metal roller 147 at its tip and which forms a part of the wafer holder 140 pushes up a part of the tube-pushing member 10 which pressed the tubes 8, 9 at the first position P1, and the heated wafer 41 which is held by the wafer holder 140 advances to the gap between the first position P1 and the second position P2 (between the first clamp 6 and the second clamp 7) to fuse the two tubes 8, 9. At this time, the tube-pushing member 10 is brought in a state that it is located at the evacuating position to the wafer 41. (See FIG. 23(C).) FIGS. 9 and 12 show a state that the wafer holder 140 ascends (swings) and the wafer 41 cuts the tubes 8, 9 set at the predetermined positions. On the other hand, the cam 157 rotates (See FIG. 26(B).) from a state shown in FIG. 26(A), but the first clamp 6 (the supporting table 164) is kept in a stopped state in the same manner as the second clamp 7 (the supporting table 174) shown in FIG. 25(A).

Figure 27:
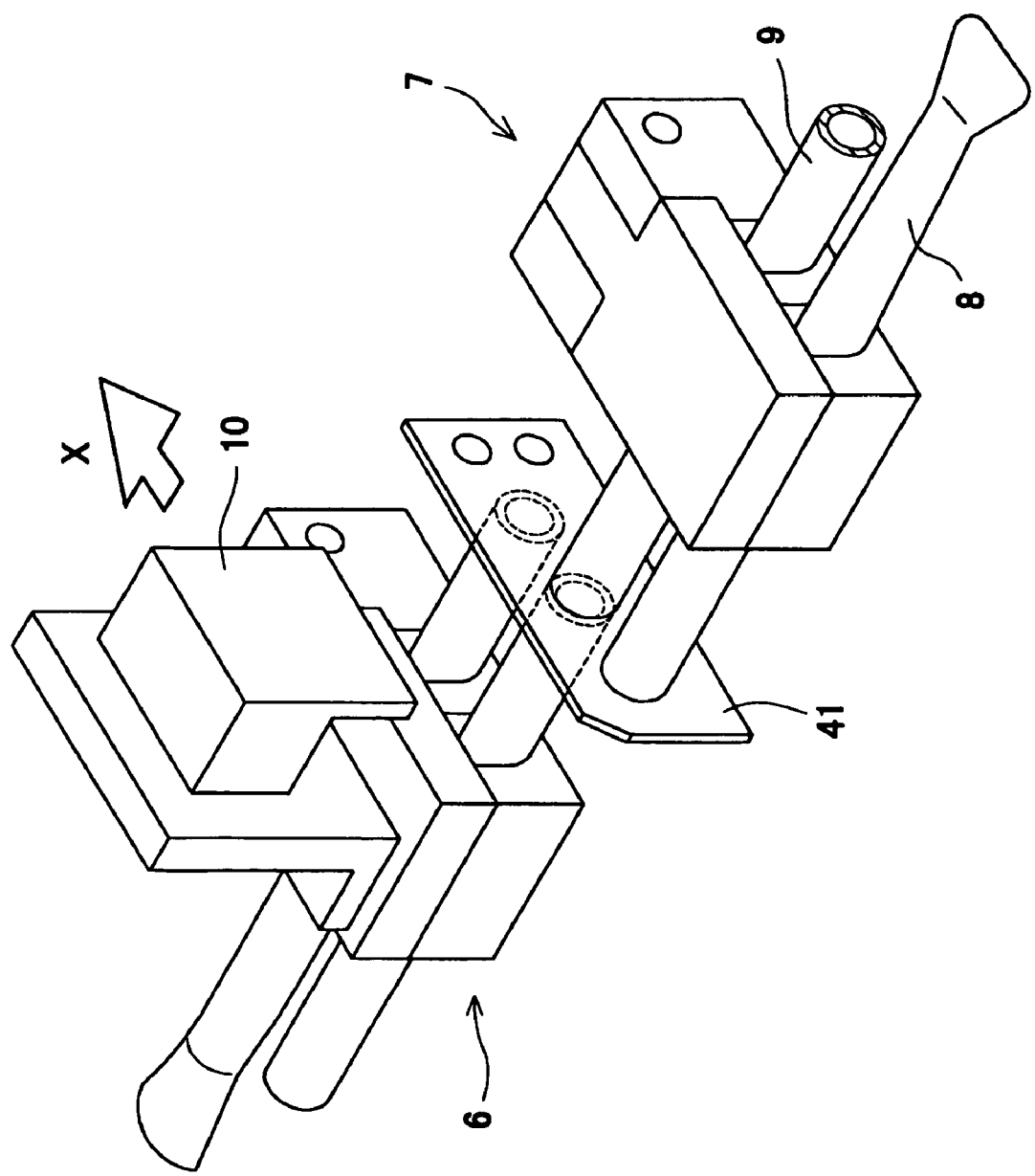
FIG. 27 is a perspective view showing operation of the main sections of the tube connecting apparatus in the tube connecting process.

The CPU 191 further continues to drive the cam motor 150. The wafer holder 140 retains a state shown in FIG. 26(B), while the first clamp 6 (the supporting table 164) moves by a predetermined distance (8 mm) in a direction of an arrow a of a left side of the FIG. 26 (C) (a direction toward an upper side of the arrow A in FIG. 3, a direction of the arrow X in FIG. 27) according to rotation of the cam 157. At this moment, the positions of the cut tubes are relatively changed and the end portions to be connected face each other. At this time, as shown in FIG. 27, the wafer 41 which has cut the tubes 8, 9 is held at a cutting position thereof in the stopped state. Further at this time, the shaft 19 of the first clamp 6 moves inside the long hole 40 of the second clamp 7 in a state that the shaft 19 is inserted in the long hole 40.

Figure 22C:
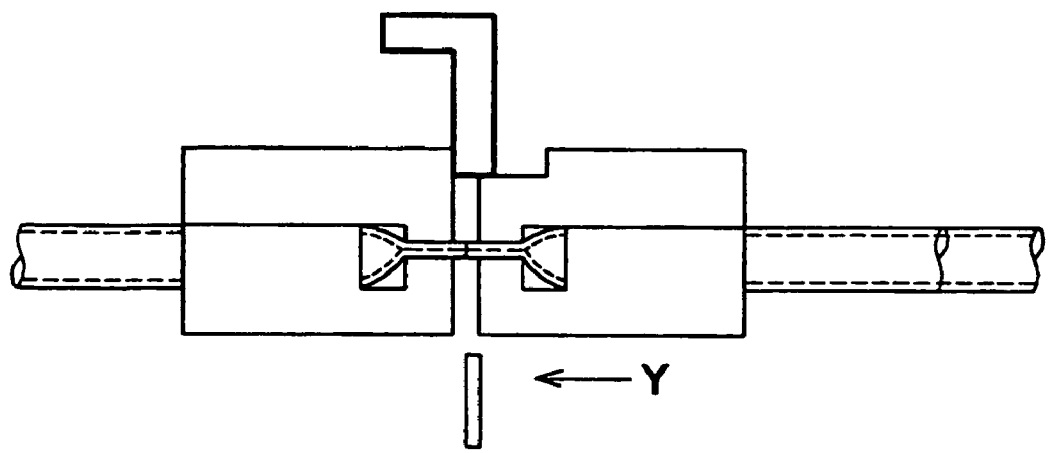

Subsequently, the wafer holder 140 swings to descend (See FIG. 26(C).) according to rotation of the cam 159, but the tube-pushing member 10 is held at the evacuating position in a stopped state (step 820). On the other hand, because the bearing 172 adjacent to the cam 158 slides along a shape of the flange portion 177, the second clamp 7 (the supporting table 174) moves by a predetermined distance (0.6 mm) in a direction of an arrow b in FIG. 25 (B) (a left direction of an arrow B in FIG. 3, a direction of an arrow Y in FIG. 22(C)).

Thus, the connecting operation of the tubes 8, 9 is finished. At this time, as shown in FIG. 6(B), the notch 198 is located at a position that faces the transmission type sensor 196, and the CPU 191 confirms a predetermined state (a state that the first clamp 6 is dislocated from the second clamp 7) to stop driving of the cam motor 150 (steps 822, 824).

In the next step 826, because the connecting operation of the tubes 8, 9 is finished, the CPU 191 renews the information with respect to the connecting process state in the EEPROM 500 from the information expressing being in a state of connecting operation to the latest information expressing being in a state of non-connecting operation. In the next step 828, the CPU 191 makes the wafer current controlling section to stop supplying electricity to the wafer 41 in order to stop heating of the wafer 41, then in the next step 830, waits until the cooling time of the wafer 41 lapses. When the cooling time lapses, the CPU 191 makes the clamp lock solenoid controlling section 506 to demagnetize the clamp lock solenoid 400 to cancel the locking state in step 832. Then, in step 834, the CPU 191 reads out the accumulated connecting number memorized in the EEPROM 500 to increase the number by 1, and makes the EEPROM 500 to memorize (renew) the increased accumulated connecting number as the latest accumulated connecting number, thereby the tube connecting subroutine is finished and the routine proceeds to step 700 in FIG. 14. Thus, execution of one tube connecting routine is completed.

When an operator cancels the engagement of the pawl member 39 against the engagement roller 30 according to the engagement mechanism 36 (or 26) by lifting the plate piece 28 provided at the tip side of the covering body 24 in order to remove the tubes that the connecting operation is finished from a main body of the apparatus, the covering body 34 (or 24) becomes an opened state as shown in FIGS. 2, 7 and 10. At this time, the covering body 24 and the covering body 34 are in a state that their relative positions are changed or dislocated, however, because the shaft 19 is inserted in the long hole 40, when the operator lifts the covering body 34 (or 24), the covering body 24 (or 34) is lifted approximately at the same time in a linking manner. Linked with the opening operation for the covering body 24, the engagement state of the tube-pushing member 10 is also canceled.

(Effects and the Like)

Next, effects and the like of the tube connecting apparatus 1 in this embodiment will be explained.

In the tube connecting apparatus 1 of this embodiment, the tube-pushing member 10 whose tip portion 12 is protruded a little more than the pressure closing member 62 of the first clamp 6 is disposed between the first clamp 6 and the second clamp 7, and the tube-pushing member 10 presses the tubes 8, 9 so as to push out the residual blood in the tubes at the pushing portion prior to pressing of the first clamp 6 and the second clamp 7 in order to exclude the blood. Accordingly, the tube connecting apparatus 1 can connect the tubes each other without being influenced by the blood in the tubes at the time of cutting and then connecting the tubes each other. Further, the tube connecting apparatus 1 can realize automatically wet-to-wet connecting between the tubes easily, uniformly and rapidly under a sterilized condition only by putting the tubes 8, 9 in which blood is contained and sealed into the grooves 22, 23, 32 and 33 and locking the covering bodies 24, 34 with the engagement mechanisms 26, 36. Because such a tube connecting apparatus has been requested to be realized from a public view especially in a medical field, an industrial value thereof seems to be extremely high.

Further, in the tube connecting apparatus 1 of this embodiment, the latest information with respect to the connecting process state of the tubes 8, 9 is renewed and memorized in the EEPROM 500 (steps 618, 626, 814 and 826). When electric power is inputted in the power-on subroutine, based upon plural information such as the information of the last connecting process state, the detecting result according to the clamp lock detecting sensor 410 and the detecting result of the wafer 41 according to the wafer position detecting sensor 421, the judgment as whether or not power supply to the tube connecting apparatus 1 was shut off during last (before power source is inputted) connecting operation of the tubes 8, 9 is made (step 602 to step 606), and the resetting is carried out (step 610) when the judgment that power supply to the tube connecting apparatus 1 was shut off during last connecting operation is made. Accordingly, the tube connecting apparatus 1 not only satisfies the demand of correctness required in the medical field since the judgment as to whether power supply was shut off is made based upon plural information, but also satisfies the demand of emergency required in the medical field since self-resetting is carried out automatically.

Namely, in the tube connecting apparatus 1 of this embodiment, the locking state is canceled (step 674) when the information with respect to the connecting process state read out from the EEPROM 500 is the information expressing being in a state of non-connecting operation (connecting is finished) or when the wafer 41 is not detected by the wafer position detecting sensor 421 (negative judgment in steps 602, 606), even if the locking state is being kept according to the self holding function of the clamp lock solenoid 400. Thus, the operator can take off the tubes 8, 9. On the other hand, when the information with respect to the connecting process state read out from the EEPROM 500 is the information expressing being in a state of connecting operation and the wafer 41 is detected by the wafer position detecting sensor 421 (affirmative judgment in steps 602, 606), the wafer 41 is heated again to fuse the tubes 8, 9 adhered to the wafer 41 and then operation is restarted to finish the connecting operation (steps 612 to 632). Thus, the operator can take off the tubes 8, 9, however, the error indication is displayed (step 632) to draw operator's attention in order to secure connecting strength and sterilized connecting. Accordingly, unlike the conventional tube connecting apparatuses, in the tube connecting apparatus 1 of this embodiment, it is not necessary to return it to a factory or the like to carry out the reset operation to an initial state. Further, the trouble due to that an operator forcibly takes off the tubes during the connecting operation and he/she gives damage to the apparatus can be prevented.

Further, in the tube connecting apparatus 1 of this embodiment, since the self-holing type clam lock solenoid 400 is used, the expanded diameter portion 405 of the clamp lock solenoid 400 engages the pawl member 39 to keep the locking state, even if power supply was shut off during tube connecting operation. Furthermore, the locking state according to the clamp lock solenoid 400 is cancelled after the cooling time of the wafer 41 lapsed (steps 630, 830). Accordingly, since an operator cannot open the covering bodies 24, 34 until the temperature of the wafer 41 cools down, the operator never touches the heated wafer 41.

Furthermore, in the tube connecting apparatus 1 of this embodiment, since the wafer 41 is exchanged by the wafer feeding mechanism 100 every time tube connecting is carried out (step 718), the connecting strength and the sterilized connection of the tubes 8, 9 are secured. On the other hand, since the latest exchange information of the wafer 41 is memorized in the EEPROM 500, and since the wafer 41 which has not been heated yet is used (the exchange information of the wafer 41 is retained as the information being exchanged as it is renewed in step 720 and the information is not judged in steps 602 to 606), even in a case that power supply was shut off during tube connecting operation because the connecting strength and the sterilized connection of the tubes 8, 9 can be secured, running costs at the time of the reset operation are reduced.

Further, in the tube connecting apparatus 1 of this embodiment, since the accumulated connecting number, the date for maintenance and the like are memorized in the EEPROM 500 and the accumulated connecting number and the date for maintenance are judged to display the results with the LCD display 192 (steps 656, 664), reliability such as connecting strength of the tubes 8, 9 required to the tube connecting apparatus 1 can be secured in advance.

Further, in the tube connecting apparatus 1 of this embodiment, the piece to be detected 119 of the wafer feeding member 115 which is located at the wafer feeding start position is detected by the transmission type sensor 132, and from the wafer feeding start position, the moving amount of the wafer feeding member 115 is detected by the revolving plate 130 and the transmission type sensor 131. Accordingly, a feeding amount (feed) of the wafer 41 can be detected precisely. Furthermore, since the feeding malfunction is judged when the actually detected number of pulses is more than the predetermined number of pulses, detection accuracy of the feeding malfunction of the wafer 41 can be improved.

Furthermore, in the tube connecting apparatus 1 of this embodiment, since the structure that the bearing 172 is capable of advancing into the notched portion 178 when the feeding malfunction of the wafer 41 caused is employed, an operator can cancel the feeding malfunction of the wafer 41 by moving the second clamp 7 to the evacuating position. Conventionally, when this type of error was occurred, the apparatus was returned to a factory as malfunction of the apparatus to remove the wafer which caused the feeding malfunction through disassembling the apparatus. However, according to the tube connecting apparatus 1, since an operator can easily carry out error cancellation due to the feeding malfunction of the wafer, operability and reliance to the apparatus can be improved.

Further, in the tube connecting apparatus 1 of this embodiment, since the wafer feeding mechanism 100 is stopped when the full state of the waste box 142 is detected by the transmission type sensor 143, even if automatic thrusting (feeding) structure for the wafer(s) is employed, the wafer jammed by the following wafer at the conveying path can be prevented. Furthermore, in the tube connecting apparatus 1, whether or not the first clamp 6 and the second clamp 7 can hold the tubes 8, 9 in parallel with each other is judged according to the transmission type sensor 195, and when the clamps are not parallel (not in the initial positions), the apparatus is not started as it is but the apparatus is started after the first clamp 6 and second clamp 7 are returned to the appropriate initial positions according to pushing of the reset switch 194. Accordingly, regular cutting and connecting operation can be always secured.

Moreover, in the tube connecting apparatus 1 of this embodiment, since the shaft 19 of the first clamp 6 can be inserted into the long hole 40 of the second clamp 7, not only in a state that the first clamp 6 and the second clamp 7 are located at the initial positions (a time of setting the tubes) but also in a state that relative positions thereof are changed (a time of finishing connecting the tubes), when either one of the covering body 24 of the first clamp 6 or the covering body 34 of the second clamp 7 is opened/closed, another of the covering body 24 of the first clamp 6 or the covering body 34 of the second clamp 7 is opened/closed approximately at the same time in a linking manner. Accordingly, operability or handling efficiency is improved. Further, in the tube connecting apparatus 1, the cam structure is employed instead of the conventional movement mechanism(s) which moves directly the first clamp 6 and the second clamp 7 in the X,Y directions such as an X,Y table or the like. Accordingly, downsizing of the apparatus per se can be realized.

Incidentally, in this embodiment, an example that the clamp lock solenoid 400 is disposed at the side of the second clamp 7 and the wafer position detecting sensor 421 is disposed at the side of the first clamp 6 was shown. However, the present invention is not limited to such disposition. The clamp lock solenoid 400 may be disposed at the side of the first clamp 7 and the wafer position detecting sensor 421 may be disposed at the side of the second clamp 6.

Further, in this embodiment, a structure that the two kinds of coils are mounted on the clamp lock solenoid 400 and that each of the coils are charged with electricity respectively at the time of moving the plunger 404 in different directions was exemplified, however, a clamp lock solenoid of which the coil is common may be used by changing a direction of current such that plus/minus of the coil is connected reversibly.

Furthermore, in this embodiment, the EEPROM 500 was exemplified as a non-volatile memory, however, the present invention is not limited to the same. An EPROM, a flash memory or a magnetic memory and the like such as a core memory or the like may be used. Further, in this embodiment, an example that the EEPROM 500 is connected to an internal bus of the controlling unit 190 via the external bus was shown, however, the present invention is not limited to this. The non-volatile memory may be disposed integrally with the CPU, ROM and RAM such that it can be connected by an internal bus.

Moreover, in this embodiment, an example that, by using the wafer position detecting sensor 421 and the shield plate 420 fixed to (provided integrally with) the wafer holder 140, the wafer position detecting sensor 421 detects the wafer holder 140 in a state that the shield plate 420 shields the light path of the wafer position detecting sensor 421 when the wafer holder 140 is rotated to ascend such that the wafer 41 is located at the cutting position at which the wafer 41 cuts the tubes 8, 9, was shown. However, to the contrary, a structure that the wafer holder 140 (wafer 41) is located at a downward initial position (non-cutting position) to detect the wafer holder 140 by shielding the light path of the wafer position detecting sensor 421 with the shielding plate 420 (When the wafer holder 140 ascends to locate the wafer 41 at the cutting position for cutting the tubes 8, 9, the wafer position detecting sensor 421 does not detect the wafer holder 140 because the light path of the wafer position detecting sensor is not shielded by the shield plate 420 but is transmitted.) may be employed. In this case, related judgments and controlling of operation may be changed appropriately.

Furthermore, in this embodiment, an example that connecting of the tubes in which blood is contained and sealed each other was shown, however, the present invention is not restricted to this. The present invention may be applied either in a case of connecting between a tube in which blood is contained and an empty tube or in a case of connecting between empty tubes in which blood is not contained; both have been carried out conventionally. Further, in this embodiment, an example that the long hole 40 is formed at the second clamp 7 was shown, however, the present invention is not confined to this. A convex shaped portion may be formed at a lower side of the plate piece 38 of the second clamp 7, and the shaft 19 and the long hole 40 respectively provided at the first clamp 6 and the second clamp 7 may be provided reversibly.

Further, in this embodiment, the tube connecting apparatus which connects the two tubes in which blood is contained and sealed was shown. However, the present invention is not restricted to the same. It is also applicable to a tube connecting apparatus which connects three tubes or more, or a tube connecting apparatus which connects tubes in which liquid other than blood is contained and sealed properly each other.

Moreover, in this embodiment, a structure that the wafer holder 140 can hold two wafers was exemplified, however, the present invention is not limited to the same. The wafer holder may hold a single wafer, or, three wafers or more.

Furthermore, in this embodiment, the saw-shaped pressure closing members 61, 62, 71, 72 and the saw-shaped tube-pushing member 10 were explained. However, since it is sufficient for these members to have a function for pushing out and excluding blood in the tubes 8, 9, they may press and close the tubes 8, 9, for example, at their horizontal faces. Further, the wafer 41 is not limited to the self-heating typed one. For example, the wafer may have a structure heated by a heat source such as an electric heater.

Moreover, in this embodiment, an example that, in the power-on subroutine (See FIG. 15.), when electric power is inputted, the CPU 191 judges as to whether power supply was shut off during last tube connecting operation based upon the information with respect to the connecting process information memorized in the EEPROM 500, the detecting result according to the clamp lock detecting sensor 410 and the detecting result of wafer 41 according to the wafer position detecting sensor 421 was shown (step 602 to step 606), however, the present invention is not limited to this. The power-on subroutine may lack one or both of the steps 602, 604, or, one or both of the steps 604, 606. For example, in a case that the routine lacks the step 602, the EEPROM 500 may be unnecessary and the CPU 191 may judge as to whether power supply was shut off only by the detecting information according to the wafer position detecting sensor 421. Further, in this embodiment, a typical example that power supply was shut off was exemplified, however, the present invention is not restricted to this. The present invention is applicable to a case that the tube connecting apparatus 1 has a halt or restarts even if power supply is not shut off.

And, in this embodiment, an example that a memory capacity of the EEPROM 500 is made small by setting the information with respect to connecting process state of the tubes 8, 9 or the exchange information of the wafer 41 to one bit and by renewing the information with respect to the latest connecting process state or the exchange state, the present invention is not limited to this. For example, a storage area for the information with respect to the connecting process state and the exchange information is set, the EEPROM 500 memorizes the information with respect to the connecting process state, the exchange information and information for identifying the latest information added thereto sequentially without deleting the previous information with respect to the connecting process state or the previous exchange information, and the EEPROM 500 may read out the latest information with respect to the connecting process state and the latest exchange information according to the information for identifying the latest information. In this case, since the storage area for memorizing the information with respect to the connecting process state and the exchange information is set, data overflow in the order of older information.

Description of Numerals 1 tube connecting apparatus
6 first clamp (holding section)
7 second clamp (holding section)
8, 9 tube
41 wafer (cutting plate)
100 wafer feeding mechanism (cutting plate conveying section)
132, 133 transmission type sensor (cutting plate conveying section detecting sensor)
140 wafer holder (cutting section)
145 electrode portion
150 cam motor (a part of a holding section movement unit, a part of a cutting section movement unit)
156 driving shaft (a part of a holding section movement unit, a part of a cutting section movement unit)
159 cam (a part of a cutting plate movement unit)
190 controlling section (a part of a controlling section)
192 LCD display (display section)
195, 196 transmission type sensor (position detecting sensor)
200 drive-conveying mechanism (a part of a holding section movement unit, a part of a cutting section movement unit, a part of a cutting plate conveying section)
400 clamp lock solenoid (engagement section)
410 clamp lock detecting sensor (holding section lock sensor)
421 wafer position detecting sensor (cutting section detecting sensor)

What is claimed is:

1. A tube connecting apparatus, comprising:
a holding section which holds at least two flexible tubes to press them to a flat state;
a cutting section which cuts the tubes held in a flat state by the holding section;
an electrode section for supplying electric power for heating to the cutting section;
a cutting section movement unit which moves the cutting section between a tube cutting position and a tube non-cutting position;
a cutting section detecting sensor which detects the cutting section moved by the cutting section movement unit;
a holding section movement unit which moves the holding section to change relative positions of the cut tubes such that end portions to be connected contact closely each other;
a controlling section which controls power supply to the electrode section as well as movement of the cutting section movement unit and the holding section movement unit; and
a display section for displaying information,
wherein the controlling section comprises a non-volatile memory which memorizes information expressing that the apparatus is in a connecting operation state in which the end portions of the cut tubes are being connected, and
wherein the controlling section is programmed to judge, when power is supplied, that a reset operation is necessary when the information memorized in the non-volatile memory is information expressing that the apparatus is in the connecting operation state, and executes the reset operation during which the cutting section is heated again, the connecting operation is restarted to finish the connecting operation, and an error indication is displayed on the display section.

2. A tube connecting apparatus according to claim 1, wherein
when the information memorized in the non-volatile memory is information expressing that the apparatus is in a connecting operation state, and, when the cutting section detecting sensor detects the cutting section moved to the tube cutting position, the controlling section is programmed to judge that the reset operation is necessary and executes the reset operation.

3. A tube connecting apparatus according to claim 1, further comprising:
an engagement section which engages at least a part of the holding section to prohibit the holding section from opening movement out of the pressing state of the tubes; and
a holding section lock sensor which detects an engagement state of the engagement section against the holding section,
wherein when the information memorized in the non-volatile memory is information expressing that the apparatus is in a connecting operation state, and, when the cutting section detecting sensor detects the cutting section moved to the tube cutting position and the holding section lock sensor detects the holding section engaged with the engagement section, the controlling section is programmed to judge that the reset operation is necessary and executes the reset operation.

4. A tube connecting apparatus according to claim 1, further comprising a position detecting sensor which detects that the holding section moved by the holding section movement unit reaches a connection finish position for contacting closely the end portions of the cut tubes each other,
wherein when the position detecting sensor detects that the holding section reaches the connection finish position, the controlling section drives the non-volatile memory to memorize information expressing that the apparatus is in a non-connecting operation state.

5. A tube connecting apparatus according to claim 1, further comprising:
a cutting plate which is held by the cutting section replaceably; and
a cutting plate conveying section which conveys the cutting plate to the cutting section replaceably,
wherein the non-volatile memory is capable of memorizing exchange information of the cutting plate.

6. A tube connecting apparatus according to claim 5, further comprising a cutting plate conveying section detecting sensor which detects the cutting plate conveying section,
wherein when the cutting plate conveying section detecting sensor detects the cutting plate conveying section, the controlling section drives the non-volatile memory to memorize information expressing the cutting plate being exchanged as the exchange information of the cutting plate.

7. A tube connecting apparatus according to claim 5, further comprising:
an engagement section which engages at least a part of the holding section to prohibit the holding section from opening movement out of the pressing state of the tubes; and
a holding section lock sensor which detects an engagement state of the engagement section against the holding section,
wherein when the information memorized in the non-volatile memory is information expressing that the apparatus is in a non-connecting operation state, and, when the holding section lock sensor detects the holding section engaged with the engagement section, the controlling section drives the non-volatile memory to memorize information expressing the cutting plate being unexchanged as the exchange information of the cutting plate.

8. A tube connecting apparatus according to claim 3, wherein the engagement section is a self-holding type solenoid into which a permanent magnet and a plunger are accommodated.

9. A tube connecting apparatus according to claim 5, wherein when the information memorized in the non-volatile memory is information expressing that the apparatus is in a non-connecting operation state, and, when the exchange information of the cutting plate memorized in the non-volatile memory is information expressing the cutting plate being unexchanged, the controlling section controls the cutting plate conveying section to convey the cutting plate to the cutting section.

* * * * *